(12) United States Patent
Yamaguchi et al.

(10) Patent No.: US 12,096,983 B2
(45) Date of Patent: Sep. 24, 2024

(54) OPHTHALMIC IMAGING APPARATUS, CONTROLLING METHOD OF THE SAME, AND RECORDING MEDIUM

(71) Applicant: Topcon Corporation, Tokyo (JP)

(72) Inventors: Tatsuo Yamaguchi, Warabi (JP); Ryoichi Hirose, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 748 days.

(21) Appl. No.: 17/198,299

(22) Filed: Mar. 11, 2021

(65) Prior Publication Data

US 2021/0196116 A1 Jul. 1, 2021

Related U.S. Application Data

(63) Continuation of application No. PCT/JP2019/031200, filed on Aug. 7, 2019.

(30) Foreign Application Priority Data

Sep. 12, 2018 (JP) .................................. 2018-170374

(51) Int. Cl.
*A61B 3/10* (2006.01)
*A61B 3/00* (2006.01)
(Continued)

(52) U.S. Cl.
CPC ............ *A61B 3/102* (2013.01); *A61B 3/0025* (2013.01); *A61B 3/14* (2013.01); *A61B 3/18* (2013.01)

(58) Field of Classification Search
CPC ....... A61B 3/0025; A61B 3/102; A61B 3/113; A61B 3/12; A61B 3/14; A61B 3/18;
(Continued)

(56) References Cited

U.S. PATENT DOCUMENTS

| 2011/0234975 A1 | 9/2011 | Hirose |
| 2013/0301008 A1 | 11/2013 | Srivastava et al. |

(Continued)

FOREIGN PATENT DOCUMENTS

| JP | 2010-151704 A | 7/2010 |
| JP | 2015-85043 A | 5/2015 |

(Continued)

OTHER PUBLICATIONS

Japanese Office Action issued Jan. 17, 2023 in corresponding Japanese Patent Application No. 2018-170374 (with machine-generated English translation), 14 pages.

(Continued)

*Primary Examiner* — Jack Dinh
(74) *Attorney, Agent, or Firm* — XSENSUS LLP

(57) ABSTRACT

In an ophthalmic imaging apparatus of some aspect examples, a data acquiring unit acquires data by applying an OCT scan to an eye. An image constructing unit constructs an image from the data acquired. A focal position changing unit is provided to the measurement arm. A scan controller controls the data acquiring unit according to a scan pattern including first and second partial patterns that are continuous patterns for central and peripheral regions of an OCT scan application area, respectively. A focus controller controls the focal position changing unit such that a first focal position is applied in parallel with an OCT scan of at least part of the first partial pattern and a second focal position is applied in parallel with an OCT scan to at least part of the second partial pattern.

11 Claims, 19 Drawing Sheets

(51) Int. Cl.
*A61B 3/14* (2006.01)
*A61B 3/18* (2006.01)

(58) Field of Classification Search
CPC ............ G01B 9/02063; G01B 9/02077; G01B 9/02091; G01B 2290/65
See application file for complete search history.

(56) References Cited

U.S. PATENT DOCUMENTS

| | | |
|---|---|---|
| 2016/0317029 A1 | 11/2016 | Srivastava et al. |
| 2017/0065171 A1 | 3/2017 | Satake et al. |
| 2017/0087019 A1 | 3/2017 | Gonzalez et al. |
| 2017/0227350 A1 | 8/2017 | Sarunic et al. |
| 2019/0059720 A1 | 2/2019 | Kubota |

FOREIGN PATENT DOCUMENTS

| | | |
|---|---|---|
| JP | 2015-515894 A | 6/2015 |
| JP | 2017-47110 A | 3/2017 |
| JP | 2017-47113 A | 3/2017 |
| JP | 2017-86311 A | 5/2017 |
| JP | 2017-153543 A | 9/2017 |
| WO | 2001/001849 A1 | 1/2001 |

OTHER PUBLICATIONS

EESR dated May 10, 2022 issued for corresponding European Patent Application No. 19860340.9.
International Search Report and Written Opinion mailed on Oct. 15, 2019, received for PCT Application PCT/JP2019/031200 Filed on Aug. 7, 2019, 11 pages including English Translation.
Polans et al., "Wide-Field Optical Model of the Human Eye With Asymmetrically Tilted and Decentered Lens That Reproduces Measured Ocular Aberrations", Optica, vol. 2, No. 2, Feb. 2015, pp. 124-134.
Japanese Office Action issued Aug. 9, 2022 in corresponding Japanese Patent Application No. 2018-170374 (with machine-generated English translation), 12 pages.
Office Action issued Nov. 21, 2023 in corresponding Japanese Patent Application No. 2022-190238 with machine English translation.
Communication pursuant to Article 94(3) EPC issued Mar. 4, 2024, in corresponding European Patent Application No. 19860340.9, 8pp.
Japanese Decision of Dismissal of Amendment and Decision of Refusal issued Apr. 23, 2024, in corresponding Japanese Patent Application No. 2022-190238, 20pp.

OPHTHALMIC IMAGING APPARATUS, CONTROLLING METHOD OF THE SAME, AND RECORDING MEDIUM

CROSS-REFERENCE TO RELATED APPLICATIONS

The present application is a continuation application of International Patent Application No. PCT/JP2019/031200, filed Aug. 7, 2019, claiming priority to Japanese Patent Application No. 2018-170374, filed Sep. 12, 2018, both of which are herein incorporated by reference in their entirety.

BACKGROUND OF THE INVENTION

Importance of diagnostic imaging and image analysis is increasing in ophthalmic examinations. In particular, the application of optical coherence tomography (OCT) to ophthalmology is encouraging this trend. The OCT enables three dimensional imaging as well as three dimensional structural analysis and functional analysis of a subject's eye, and serves an effective role for acquiring distributions of various measurement values, for example.

In recent years, the widening of OCT scan area, in other words, the enlargement of the angle of view of OCT (OCT scan angle), has been advanced. For example, apparatuses have been developed in which the deflection angle of an optical scanner (e.g., a galvano mirror scanner) is increased as well as the structure, control, and imaging are optimized accordingly in order to achieve wide area scanning from the central part to the peripheral part of the eye fundus (see, for example, Japanese Unexamined Patent Application Publication No. 2017-086311 and Japanese Unexamined Patent Application Publication No. 2017-047113).

When applying an OCT scan (generally a raster scan) to a wide area of the eye fundus, the image quality deteriorates especially in an area away from the central part of the eye fundus (referred to as a peripheral part) due to the influence of aberration of the ocular optical system (the optical system of the eyeball). This is due to the fact that the aberration of the eyeball is larger for the peripheral part than for the central part of the eye fundus (see, for example, JAMES POLANS, et al., "Wide-field optical model of the human eye with asymmetrically tilted and decentered lens that reproduces measured ocular aberrations", Optica, February 2015, Vol. 2, No. 2, pp. 124-134).

Performing focus control may be conceived as a possible solution to such image quality deterioration. However, the speed of focus control is considerably slower than the speed of OCT scanning (e.g., the repetition rate of A-scans). Therefore, performing focus control while applying a raster scan at high speed to a wide area of the eye fundus may be unrealistic.

BRIEF SUMMARY OF THE INVENTION

An object of the present invention is to acquire a high-quality OCT image while performing a wide angle OCT scan at high speed.

The first aspect of some embodiment examples is an ophthalmic imaging apparatus that includes: a data acquiring unit configured to acquire data by applying an optical coherence tomography (OCT) scan to a subject's eye; an image constructing unit configured to construct an image from the data acquired by the data acquiring unit; a focal position changing unit provided to an optical path of measurement light projected onto the subject's eye by the data acquiring unit; a scan controller configured to control the data acquiring unit according to a scan pattern that includes a first partial pattern and a second partial pattern, the first partial pattern being a continuous scan pattern for a central region of an OCT scan application area and the second partial pattern being a continuous scan pattern for a peripheral region; and a focus controller configured to control the focal position changing unit such that a first focal position is applied in parallel with an application of an OCT scan to at least a part of the first partial pattern and a second focal position different from the first focal position is applied in parallel with an application of an OCT scan to at least a part of the second partial pattern.

The second aspect of some embodiment examples is the ophthalmic imaging apparatus of the first aspect, in which the scan pattern includes a curved scan pattern defined in a polar coordinate system whose origin is located at a center of the OCT scan application area.

The third aspect of some embodiment examples is the ophthalmic imaging apparatus of the second aspect, in which the curved scan pattern is one of a spiral scan pattern directed from the center to an outer edge of the OCT scan application area and a spiral scan pattern directed from the outer edge to the center of the OCT scan application area.

The fourth aspect of some embodiment examples is the ophthalmic imaging apparatus of the second or third aspect, in which the image constructing unit constructs an image defined in the polar coordinate system from data acquired by an OCT scan applied to the subject's eye according to the curved scan pattern, and converts the image defined in the polar coordinate system to an image defined in a three dimensional Cartesian coordinate system.

The fifth aspect of some embodiment examples is the ophthalmic imaging apparatus of any of the first to fourth aspects, in which a first focal length corresponding to the first focal position is longer than a second focal length corresponding to the second focal position.

The sixth aspect of some embodiment examples is the ophthalmic imaging apparatus of any of the first to fifth aspects, in which the data acquiring unit applies a preparatory OCT scan to the subject's eye prior to an OCT scan according to the scan pattern, and the image constructing unit constructs a preparatory image from data acquired by the preparatory OCT scan. In addition, the ophthalmic imaging apparatus further includes a parameter setting processor configured to perform setting of one or more focus control parameters based on the preparatory image constructed by the image constructing unit, and the focus controller then performs control of the focal position changing unit according to the one or more focus control parameters set by the parameter setting processor.

The seventh aspect of some embodiment examples is the ophthalmic imaging apparatus of the sixth aspect, in which the one or more focus control parameters include a focal position change range that includes the first focal position and the second focal position.

The eighth aspect of some embodiment examples is the ophthalmic imaging apparatus of the sixth or seventh aspect, in which the one or more focus control parameters include at least one of movement speed and movement acceleration of a focal position.

The ninth aspect of some embodiment examples is the ophthalmic imaging apparatus of any of the first to eighth aspects, further including: a photographing unit configured to perform repetitive photographing of the subject's eye; and a movement detecting processor configured to detect movement of the subject's eye by analyzing a time series image acquired by the photographing unit. In addition, the data acquiring unit includes an optical scanner configured to deflect light for OCT scanning, and the scan controller controls the optical scanner based on an output from the movement detecting processor while controlling the data acquiring unit according to the scan pattern.

The tenth aspect of some embodiment examples is a method of controlling an ophthalmic imaging apparatus. The ophthalmic imaging apparatus includes a data acquiring unit, an image constructing unit, and a focal position changing unit. The data acquiring unit is configured to acquire data by applying an optical coherence tomography (OCT) scan to a subject's eye, the image constructing unit is configured to construct an image from the data acquired by the data acquiring unit, and the focal position changing unit is provided to an optical path of measurement light projected onto the subject's eye by the data acquiring unit. The method of controlling an ophthalmic imaging apparatus includes: a scan control step of controlling the data acquiring unit according to a scan pattern that includes a first partial pattern and a second partial pattern, the first partial pattern being a continuous scan pattern for a central region of an OCT scan application area and the second partial pattern being a continuous scan pattern for a peripheral region; and a focus control step of controlling the focal position changing unit such that a first focal position is applied in parallel with an application of an OCT scan to at least a part of the first partial pattern and a second focal position different from the first focal position is applied in parallel with an application of an OCT scan to at least a part of the second partial pattern.

The eleventh aspect of some embodiment examples is a program that causes a computer to execute the method of controlling the ophthalmic imaging apparatus of the tenth aspect.

The twelfth aspect of some embodiment examples is a computer-readable non-transitory recording medium that stores the program of the eleventh aspect.

According to some embodiment examples, a high-quality OCT image can be acquired while performing a wide angle OCT scan at high speed.

DETAILED DESCRIPTION OF THE INVENTION

Figure 1:
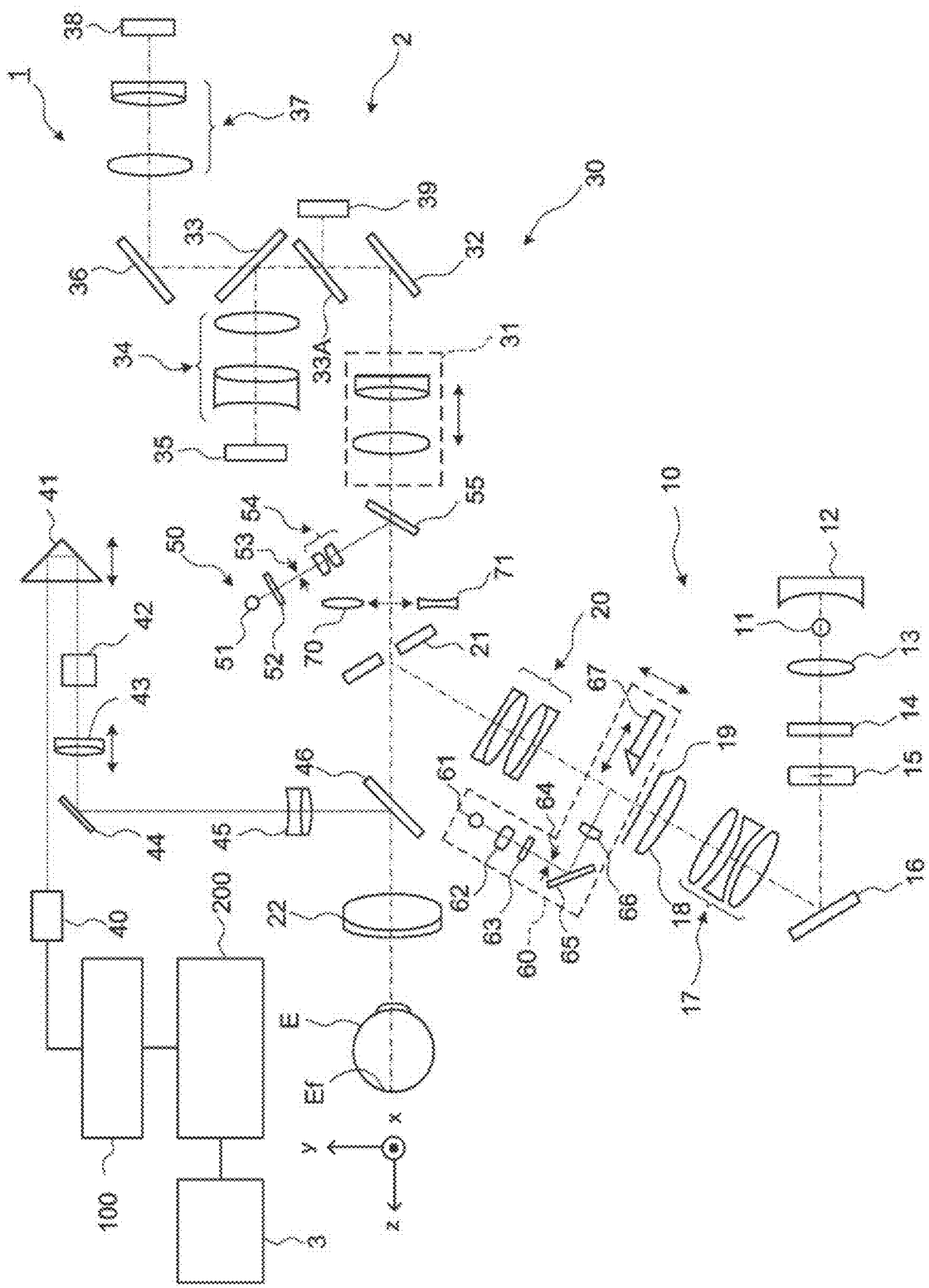
FIG. 1 is a schematic diagram illustrating an example of the configuration of the ophthalmic imaging apparatus according to the embodiment example.

The present disclosure describes, in detail with referring to the drawings, some embodiment examples of an ophthalmic imaging apparatus, a method of controlling an ophthalmic imaging apparatus, a program, and a recording medium relating to the present invention. Any of the disclosures of the documents cited in the present specification and/or any other known techniques or technologies can be incorporated into the embodiment examples described herein. In addition, "image data" and an "image" based thereon are not distinguished from one another unless otherwise mentioned. Likewise, a "site" of the subject's eye and an "image" thereof are not distinguished from one another unless otherwise mentioned.

An ophthalmic imaging apparatus according to some embodiment examples is capable of performing imaging and measurement of the fundus of a living eye with Fourier domain OCT (e.g., swept source OCT). The types of OCT techniques applicable to embodiments are not limited to swept source OCT, and some embodiment examples may employ spectral domain OCT or time domain OCT, for example. Further, parts of a living eye to which OCT scanning are to be applied are not limited to an eye fundus, and some embodiment examples may apply OCT scanning to any site of a living eye such as an anterior eye segment or a vitreous body.

Some embodiment examples may be capable of processing images acquired by a modality other than OCT. For example, some embodiment examples may be capable of processing images acquired using any of a fundus camera, a scanning laser ophthalmoscope (SLO), a slit lamp microscope, and an ophthalmic surgical microscope. An ophthalmic imaging apparatus according to some embodiment examples may include any of a fundus camera, an SLO, a slit lamp microscope, and an ophthalmic surgical microscope.

The images of the subject's eye that can be processed by some embodiment examples may include an image obtained by analyzing an image acquired by a modality of any kind. Examples of such an analyzed image include the following: a pseudo-colored image (e.g., a segmented pseudo-color image); an image consisting only of a part of the original image (e.g., a segment image); an image representing the thickness distribution of a tissue obtained from analysis of an OCT image (e.g., a layer thickness map or a layer thickness graph); an image representing the shape of a tissue (e.g., a curvature map); and an image representing the distribution of lesions (e.g., a lesion map).

<Configurations>

The ophthalmic imaging apparatus 1 of an embodiment example shown in FIG. 1 includes the fundus camera unit 2, the OCT unit 100 and the arithmetic and control unit 200. The fundus camera unit 2 is provided with optical systems and mechanisms for acquiring front images of a subject's eye. The OCT unit 100 includes part of optical systems and part of mechanisms for performing OCT. Another part of the optical systems and another part of the mechanisms for performing OCT is provided in the fundus camera unit 2. The arithmetic and control unit 200 includes one or more processors that perform various calculations, operations, and controls. In addition to them, the ophthalmic imaging apparatus 1 may also include arbitrary kinds of elements such as a member for supporting the face of the subject (e.g., a chin rest and/or a forehead rest), and/or arbitrary kinds of units such as a lens unit for switching the sites to which OCT is applied. An example of such a lens unit is an attachment for anterior eye segment OCT.

In the present specification, the term "processor" is used to mean, for example, a circuit (circuitry) such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. For example, a processor of an embodiment example loads and executes a program stored in a storage circuit or a storage device, thereby implementing functions according to the embodiment example.

<Fundus Camera Unit 2>

The fundus camera unit 2 is provided with optical systems for photographing the fundus Ef of the subject's eye E. Images of the fundus Ef (referred to as fundus images, fundus photographs, or the like) obtained by the fundus camera unit 2 are front images such as observation images and photographed images. An observation image is obtained, for example, by capturing a moving image using near-infrared light. The observation image is used in operations such as alignment, focusing, and tracking. A photographed image is, for example, a still image obtained by using visible or infrared flash light.

The fundus camera unit 2 includes the illumination optical system 10 and the photographing optical system 30. The illumination optical system 10 projects illumination light onto the subject's eye E. The photographing optical system 30 detects the return light of the illumination light from the subject's eye E. The measurement light incident from the OCT unit 100 is directed to the subject's eye E through the optical path in the fundus camera unit 2. In addition, the return light of the measurement light from the subject's eye E is directed to the OCT unit 100 through the same optical path.

The light output from the observation light source 11 of the illumination optical system 10 (referred to as observation illumination light) is reflected by the concave mirror 12, passes through the condenser lens 13, and becomes near-infrared light after passing through the visible cut filter 14. Further, the observation illumination light is once converged at a location near the photographing light source 15, reflected by the mirror 16, and passes through the relay lens system 17, the relay lens 18, the diaphragm 19, and the relay lens system 20. Then, the observation illumination light is reflected on the peripheral part (i.e., the surrounding area of the aperture part) of the aperture mirror 21, penetrates the dichroic mirror 46, and refracted by the objective lens 22, thereby illuminating the subject's eye E (the fundus Ef). The return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the return light passes through the half mirror 33A, is reflected by the dichroic mirror 33, and forms an image on the light receiving surface of the image sensor 35 by the imaging lens 34. The image sensor 35 detects the return light at a predetermined frame rate (capture rate). Note that the focus (i.e., the focal position) of the photographing optical system 30 is adjusted to coincide with the fundus Ef or the anterior eye segment.

The light output from the photographing light source 15 (referred to as photographing illumination light) passes through the same route as that of the observation illumination light and is projected onto the fundus Ef. The return light of the photographing illumination light from the subject's eye E passes through the same route as that of the return light of the observation illumination light, is guided to the dichroic mirror 33, passes through the dichroic mirror 33, is reflected by the mirror 36, and forms an image on the light receiving surface of the image sensor 38 by the imaging lens 37.

The liquid crystal display (LCD) 39 displays a fixation target (i.e., a fixation target image). Part of the light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

By changing the display position of the fixation target image on the screen of the LCD 39, the fixation position of the subject's eye E by the fixation target can be changed. Examples of the fixation position includes the following: a fixation position for acquiring an image centered on the macula; a fixation position for acquiring an image centered on the optic nerve head; a fixation position for acquiring an image centered on the position that is located between the macula and the optic nerve head; and a fixation position for acquiring an image of a site far away from the macula (i.e., a periphery of the fundus). A user interface such as a graphical user interface (GUI) for designating at least one of such typical fixation positions can be provided. Further, a user interface such as a GUI for manually changing the fixation position (i.e., the display position of the fixation target) can be provided.

The configuration for presenting the fixation target, which is capable of changing the fixation position, to the subject's eye E is not limited to display devices such as an LCD. For example, a fixation matrix can be adopted in place of a display device. The fixation matrix includes a plurality of light emitting parts (e.g., light emitting diodes) that are disposed in a matrix-like arrangement (in a matrix array). In this case, the fixation position of the subject's eye E by the fixation target can be changed by lighting one (or more) of the plurality of light emitting parts in a selective manner. As another example, the fixation target that is capable of changing the fixation position can be generated by employing one or more movable light emitting parts.

The alignment optical system 50 generates an alignment indicator used for the alignment of the optical system with respect to the subject's eye E. The alignment light output from the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. The return light of the alignment light from the subject's eye E (the cornea reflection light, etc.) passes through the same route as that of the return light of the observation illumination light and is guided to the image sensor 35. Based on the received image (referred to as the alignment indicator image), manual alignment and/or automatic alignment can be performed.

As in a conventional case, the alignment indicator image of the present example includes two bright spot images whose positions change according to alignment states. When the relative position between the subject's eye E and the optical system changes in the xy direction, the two bright spot images are shifted in the xy direction in an integrated manner. When the relative position between the subject's eye E and the optical system changes in the z direction, the relative position (i.e., the distance) between the two bright spot images changes. When the distance between the subject's eye E and the optical system in the z direction matches a predetermined working distance, the two bright spot images overlap with each other. When the position of the subject's eye E matches the position of the optical system in the xy direction, the two bright spot images are presented within or near a given alignment target. When the distance between the subject's eye E and the optical system in the z direction matches the working distance, and the position of the subject's eye E matches the position of the optical system in the xy direction, the two bright spot images overlap with each other and are presented within the alignment target.

In the automatic alignment, the data processor 230 detects the positions of the two bright spot images, and the main controller 211 controls the movement mechanism 150 (described later) on the basis of the positional relationship between the two bright spot images and the alignment target. In the manual alignment, the main controller 211 displays the two bright spot images together with the observation image of the subject's eye E on the display device 241, and the user operates the movement mechanism 150 using the operation device 242 while referring to the two bright spot images displayed.

The focus optical system 60 generates a split indicator used for the focus adjustment with respect to the subject's eye E. In conjunction with the movement of the photography focusing lens 31 along the optical path of the photographing optical system 30 (referred to as the photographing optical path), the focus optical system 60 is moved along the optical path of the illumination optical system 10 (referred to as the illumination optical path). The reflection rod 67 is inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, and passes through the two-hole diaphragm 64. Then, the focus light is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. The return light of the focus light from the subject's eye E (e.g., the fundus reflection light) passes through the same route as the return light of the alignment light and is guided to the image sensor 35. Based on the image (referred to as the split indicator image), manual focusing and/or automatic focusing can be performed.

The diopter correction lenses 70 and 71 can be selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT (measurement arm). The dichroic mirror 46 reflects the light of wavelength bands used for OCT and transmits the light for fundus photography. Listed from the OCT unit 100 side, the collimator lens unit 40, the retroreflector 41, the dispersion compensation member 42, the OCT focusing lens 43, the optical scanner 44, and the relay lens 45 are arranged in the measurement arm.

The retroreflector 41 is movable in the directions of the arrows shown in FIG. 1. Thereby, the length of the measurement arm is changed. The change in the measurement arm length can be utilized for optical path length correction based on an eye axial length and for interference condition control (adjustment, regulation), for example.

Together with the dispersion compensation member 113 (described later) arranged in the reference arm, the dispersion compensation member 42 acts to equalize the dispersion characteristics of the measurement light LS and the dispersion characteristics of the reference light LR with each other.

The OCT focusing lens 43 is movable along the measurement arm in order to perform the focus adjustment of the measurement arm. The ophthalmic imaging apparatus 1 may control the movement of the photography focusing lens 31, the movement of the focus optical system 60, and the movement of the OCT focusing lens 43 in an interlocking manner.

The optical scanner 44 is placed at a position substantially optically conjugate with the pupil of the subject's eye E. The optical scanner 44 deflects the measurement light LS guided through the measurement arm. An example of the optical scanner 44 is a galvano scanner that allows two dimensional scanning. The galvano scanner includes a galvano mirror for scanning in the x direction and a galvano mirror for scanning in the y direction.

<OCT Unit 100>

Figure 2:
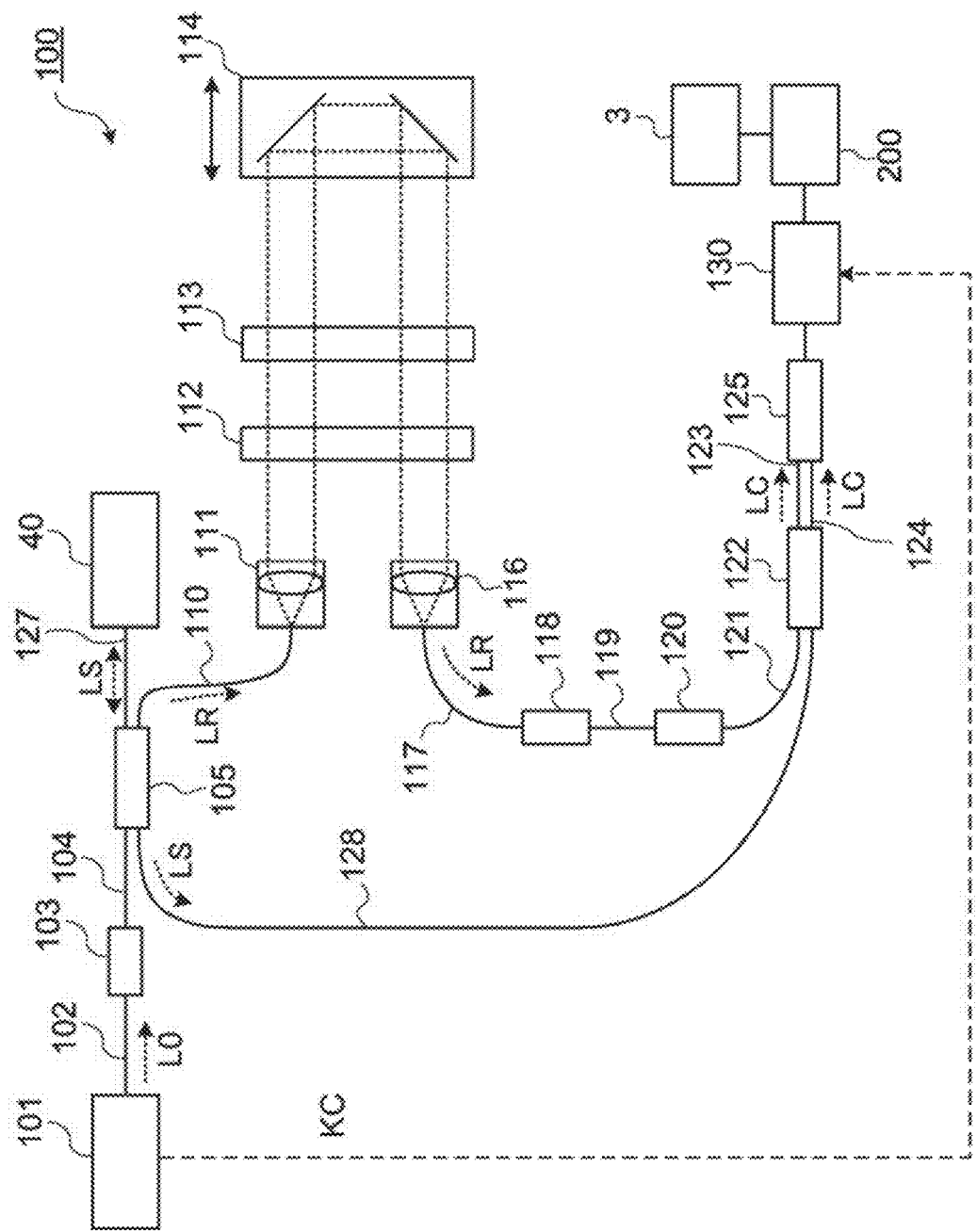
FIG. 2 is a schematic diagram illustrating an example of the configuration of the ophthalmic imaging apparatus according to the embodiment example.

As illustrated in FIG. 2, the OCT unit 100 is provided with the optical system for applying swept source OCT. The optical system includes an interference optical system. The interference optical system is configured to split the light emitted from a wavelength tunable light source (also referred to as a wavelength swept light source) into measurement light and reference light, superpose the return light of the measurement light returned from the subject's eye E with the reference light having traveled through the reference optical path to generate interference light, and detect the interference light. The result of the detection (i.e., a detection signal) obtained by the interference optical system is a signal representing a spectrum of the interference light. The detection signal is sent to the arithmetic and control unit 200.

The light source unit 101 includes, for example, a near infrared tunable laser configured to vary the wavelengths of emitted light at high speed. The light L0 output from the light source unit 101 is guided to the polarization controller 103 through the optical fiber 102, and the polarization state of the light L0 is regulated. Further, the light L0 is guided to the fiber coupler 105 through the optical fiber 104 and is split into the measurement light LS and the reference light LR. The optical path of the measurement light LS is referred to as a measurement arm, a sample arm, or the like, and the optical path of the reference light LR is referred to as a reference arm or the like.

The reference light LR is guided through the optical fiber 110 to the collimator 111, is converted into a parallel light beam, travels through the optical path length correction member 112 and the dispersion compensation member 113, and is guided to the retroreflector 114. The optical path length correction member 112 acts to match the optical path length of the reference light LR and the optical path length of the measurement light LS with each other. Together with the dispersion compensation member 42 arranged in the measurement arm, the dispersion compensation member 113 acts to equalize the dispersion characteristics of the reference light LR and the dispersion characteristics of the measurement light LS with each other. The retroreflector 114 is movable along the optical path of the reference light LR incident on the retroreflector 114. With this, the length of the reference arm is changed. The change in the reference arm length can be utilized, for example, for correction of the optical path length based on an axial length, and for interference condition control (adjustment, regulation).

After passing through the retroreflector 114, the reference light LR travels through the dispersion compensation member 113 and the optical path length correction member 112, is converted from a parallel light beam to a convergent light beam by the collimator 116, and is incident on the optical fiber 117. The reference light LR having entered the optical fiber 117 is guided to the polarization controller 118, and the polarization state of the reference light LR is regulated. The reference light LR having guided to the polarization controller 118 is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided to the collimator lens unit 40 by the optical fiber 127 and is converted to a parallel light beam. The measurement light LS, then, passes through the retroreflector 41, the dispersion compensation member 42, the OCT focusing lens 43, the optical scanner 44, and the relay lens 45, and then reaches the dichroic mirror 46. The measurement light LS is reflected by the dichroic mirror 46, is refracted by the objective lens 22, and is projected onto the subject's eye E. The measurement light LS is reflected and scattered at various depth positions of the subject's eye E. The return light of the measurement light LS returned from the subject's eye E travels along the same route as the outward way in the opposite direction, is directed to the fiber coupler 105, and then reaches the fiber coupler 122 via the optical fiber 128.

The fiber coupler 122 superposes the measurement light LS incident through the optical fiber 128 with the reference light LR incident through the optical fiber 121, to generate interference light. The fiber coupler 122 splits the generated interference light at a predetermined splitting ratio (e.g., the ratio is 1 to 1) to generate a pair of the interference light LC. The pair of the interference light LC is guided to the detector 125 respectively through the optical fibers 123 and 124.

The detector 125 includes, for example, a balanced photo diode. The balanced photodiode includes a pair of photodetectors for respectively detecting the pair of the interference light LC. The balanced photodiode outputs the difference between the pair of detection results obtained by the pair of photodetectors. The detector 125 sends the output (i.e., detection signal) to the data acquisition system (DAQ) 130.

The clock KC is supplied from the light source unit 101 to the data acquisition system 130. The clock KC is generated in the light source unit 101 in synchronization with the output timings of the respective wavelengths varied within a predetermined wavelength range by the wavelength tunable type light source. For example, the light source unit 101 splits the light L0 of each output wavelength to generate two pieces of split light, applies an optical delay to one of the two pieces of split light, superposes the two pieces of split light with each other, detects the superposed light, and generates the clock KC based on the detection result of the superposed light. The data acquisition system 130 uses the clock KC to perform the sampling of the detection signal input from the detector 125. The data acquisition system 130 sends the result of the sampling of the detection signal to the arithmetic and control unit 200.

The present example configuration is provided with both an element for changing the measurement arm length (e.g., the retroreflector 41) and an element for changing the reference arm length (e.g., the retroreflector 114 or a reference mirror); however, only one of these two elements may be provided in some other embodiment examples. An element for changing the difference between the measurement arm length and the reference arm length (i.e., an element for changing the optical path length difference) is not limited to the aforesaid elements, and may be any type of element (e.g., any type of an optical member, any type of a mechanism).

<Control System and Processing System>

Figure 3:
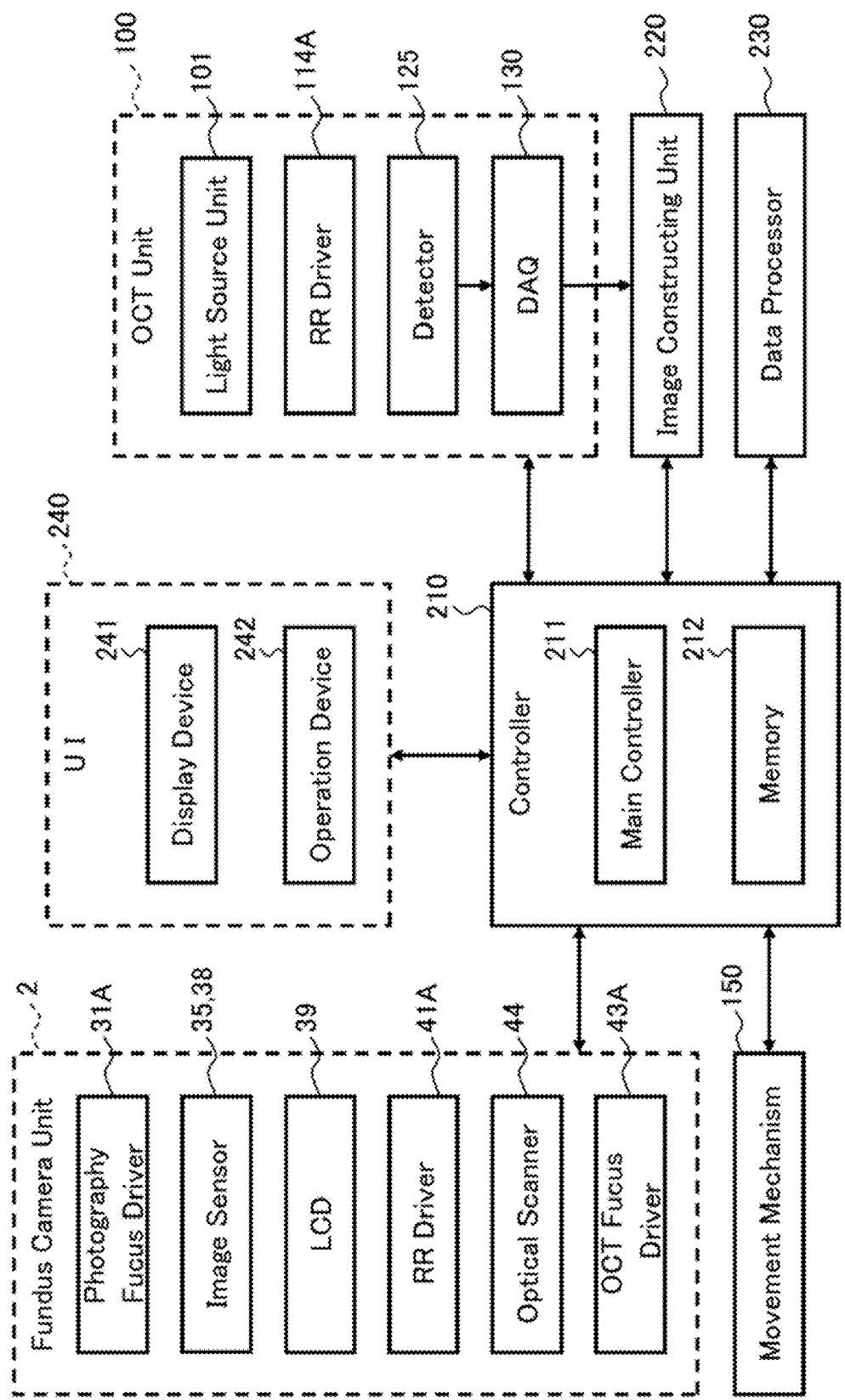
FIG. 3 is a schematic diagram illustrating an example of the configuration of the ophthalmic imaging apparatus according to the embodiment example.
Figure 4:
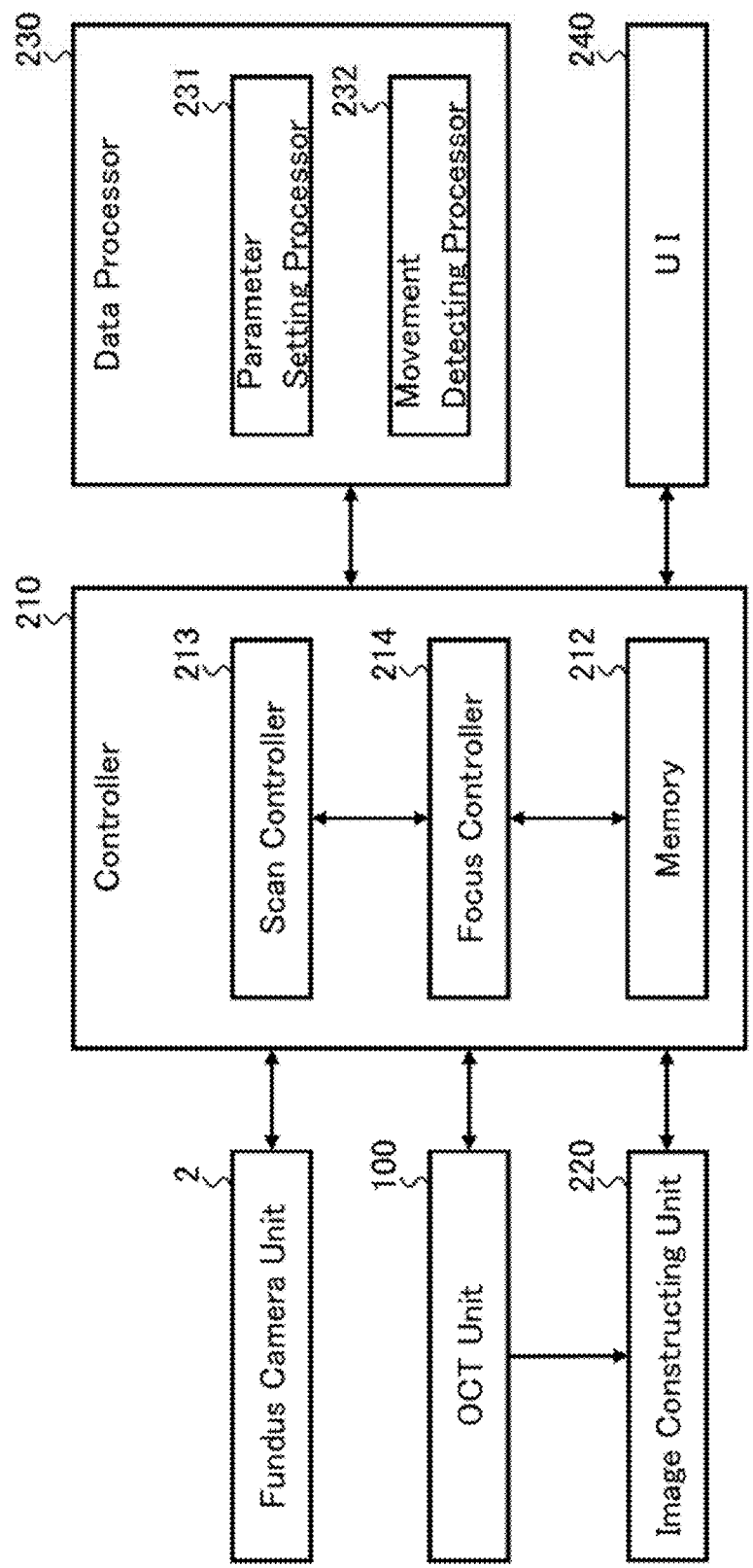
FIG. 4 is a schematic diagram illustrating an example of the configuration of the ophthalmic imaging apparatus according to the embodiment example.

FIG. 3 and FIG. 4 show an example of the configuration of the control system and the processing system of the ophthalmic imaging apparatus 1. The controller 210, the image constructing unit 220, and the data processor 230 are provided in the arithmetic and control unit 200, for example. The ophthalmic imaging apparatus 1 may include a communication device for performing data communication with an external device. The ophthalmic imaging apparatus 1 may include a drive device (e.g., a reader and/or a writer) for performing a process of reading data from a recording medium and a process of writing data into the recording medium.

<Controller 210>

The controller 210 performs various kinds of control processing. The controller 210 includes the main controller 211 and the memory 212. In addition, as shown in FIG. 4, the controller 210 of the present embodiment example includes the scan controller 213 and the focus controller 214.

<Main Controller 211>

The main controller 211 includes one or more processors and controls each element of the ophthalmic imaging apparatus 1 (including each of the elements shown in FIG. 1 to FIG. 4). The main controller 211 is implemented by the cooperation of hardware including the processors and control software.

The main controller 211 can operate the scan controller 213 and the focus controller 214 in an interlocking manner (e.g., in a synchronized manner). With this, the OCT scanning and the focus adjustment are performed in an interlocking manner (e.g., in a synchronized manner).

Under the control of the main controller 211, the photography focus driver 31A moves the photography focusing lens 31 disposed in the photographing optical path and the focus optical system 60 disposed in the illumination optical path. Under the control of the main controller 211, the retroreflector driver (RR driver, for short) 41A moves the retroreflector 41 disposed in the measurement arm. Under the control of the main controller 211, the OCT focus driver 43A moves the OCT focusing lens 43 disposed in the measurement arm. The optical scanner 44 disposed in the measurement arm operates under the control of the main controller 211. The retroreflector driver (RR driver, for short) 114A moves the retroreflector 114 disposed in the reference arm under the control of the main controller 211. Each of the aforesaid drivers includes an actuator, such as a pulse motor, that operates under the control of the main controller 211.

The movement mechanism 150 moves, for example, at least the fundus camera unit 2 in a three dimensional manner. In a typical example, the movement mechanism 150 includes the following: an x-stage movable in the +x and −x directions (i.e., left and right directions); an x-movement mechanism that moves the x-stage; a y-stage movable in the +y and −y directions (i.e., up and down directions); a y-movement mechanism that moves the y-stage; a z-stage movable in the +z and −z directions (i.e., depth direction); and a z-movement mechanism that moves the z-stage. Each of the movement mechanisms described here includes an actuator such as a pulse motor that operates under control of the main controller 211.

<Memory 212>

The memory 212 stores various kinds of data. Examples of the data stored in the memory 212 include OCT images, fundus images, subject's eye information, and control parameters.

The subject's eye information includes subject information such as the patient ID and the patient's name, identification information for the left eye and the right eye, and electronic medical record information.

A control parameter includes, for example, a parameter used for control of OCT scanning (referred to as a scan control parameter), a parameter used for focus control such as focal position control (referred to as a focus control parameter).

The scan control parameter is a parameter indicating the content of control for the optical scanner 44. Examples of the scan control parameter include a parameter indicating a scan pattern, a parameter indicating a scan rate (or scan speed), and a parameter indicating scan intervals. The scan rate is defined as, for example, an A-scan repetition rate. The scan intervals are defined as, for example, intervals between mutually adjacent A-scans, that is, arrangement intervals of scan points. A description will be given later of the scan pattern.

The focus control parameter is a parameter indicating the content of control for the OCT focus driver 43A. Examples of the focus control parameter include a parameter indicating the focal position of the measurement arm, a parameter indicating the moving speed (velocity) of the focal position, and a parameter indicating the acceleration in the movement of the focal position. The parameter indicating the focal position is, for example, a parameter indicating the position of the OCT focusing lens 43. The parameter indicating the moving speed of the focal position is, for example, a parameter indicating the moving speed of the OCT focusing lens 43. The parameter indicating the moving acceleration of the focal position is, for example, a parameter indicating the moving acceleration of the OCT focusing lens 43. The moving speed may or may not be constant. The same applies to the moving acceleration.

<Scan Controller 213>

The scan controller 213 controls the optical scanner 44 based on the scan control parameters. The scan controller 213 may further perform control of the light source unit 101. The contents of processing executed by the scan controller 213 will be described later. The scan controller 213 is included in the main controller 211. The scan controller 213 is implemented by the cooperation of hardware including a processor and scan control software.

<Focus Controller 214>

The focus controller 214 controls the OCT focus driver 43A based on the focus control parameters. The contents of processing executed by the focus controller 214 will be described later. The focus controller 214 is included in the main controller 211. The focus controller 214 is implemented by the cooperation of hardware including a processor and focus control software.

<Image Constructing Unit 220>

The image constructing unit 220 includes a processor, and constructs OCT image data of the fundus Ef based on signals (sampling data) input from the data acquisition system 130. The OCT image data is, for example, B-scan image data, that is, two dimensional cross sectional image data.

The processing for constructing OCT image data includes noise elimination (or noise reduction), filtering, fast Fourier transform (FFT), and other processes as in a conventional Fourier domain OCT. In the event where another type of OCT apparatus is used, the image constructing unit 220 performs known processing according to the OCT type employed.

The image constructing unit 220 constructs three dimensional data of the fundus Ef based on signals input from the data acquisition system 130. The three dimensional data is three dimensional image data representing a three dimensional region (i.e., a volume) of the fundus Ef. Three dimensional image data means image data in which pixel positions are defined using a three dimensional coordinate system. Stack data and volume data are examples of three dimensional image data.

Stack data is image data constructed by three dimensionally arranging a plurality of cross sectional images obtained along a plurality of scan lines, based on the positional relationship of the scan lines. In other words, stack data is image data constructed by representing a plurality of cross sectional images, which are originally defined using respectively different two dimensional coordinate systems, using a common single three dimensional coordinate system, that is, by embedding the cross sectional images in a single three dimensional space. Alternatively, stack data is image data constructed by three dimensionally arranging a plurality of pieces of A-scan data obtained respectively for a plurality of scan points arranged in a two dimensional manner (i.e., scan point array), based on the positional relationship of the scan points.

Volume data is image data whose picture elements are voxels that are arranged in a three dimensional manner. Volume data is also referred to as voxel data. Volume data is constructed by applying known interpolation, voxelization, or the like, to stack data.

The image constructing unit 220 constructs an image to be displayed, by applying rendering to three dimensional image data. Examples of applicable rendering methods include volume rendering, surface rendering, maximum intensity projection (MIP), minimum intensity projection (MinIP), and multi planar reconstruction (MPR).

The image constructing unit 220 may be configured to construct an OCT front image (also referred to as an OCT en-face image) based on three dimensional image data. For example, the image constructing unit 220 may be configured to construct projection data by projecting three dimensional image data in the z direction (A-line direction, depth direction). Further, the image constructing unit 220 may be configured to construct a shadowgram by projecting partial data of three dimensional image data in the z direction.

Partial three dimensional image data used for the shadowgram construction is set, for example, using segmentation. Segmentation is a process of specifying a partial region in an image. Typically, segmentation is used to specify an image region corresponding to a predetermined tissue of the fundus Ef. Segmentation is performed, for example, by the image constructing unit 220 or the data processor 230.

The ophthalmic imaging apparatus 1 may be capable of performing OCT angiography. OCT angiography is an imaging technique that constructs an image in which retinal blood vessels and choroidal blood vessels are emphasized. This technique is disclosed, for example, in Japanese Unexamined Patent Application Publication (Translation of PCT Application) No. 2015-515894. Generally, fundus tissues (i.e., fundus structures) do not change with time, but the blood flow inside blood vessels change with time. In OCT angiography, an image is generated by emphasizing parts (e.g., blood flow signals) in which such time-dependent changes exist. OCT angiography is also referred to as OCT motion contrast imaging. In addition, images obtained by OCT angiography are referred to as angiographic images, angiograms, motion contrast images, or the like.

When OCT angiography is performed, the ophthalmic imaging apparatus 1 repetitively scans the same region of the fundus Ef a predetermined number of times. For example, the repetitive scanning may be performed along a path between two points on a predetermined scan pattern such as a spiral scan pattern. The image constructing unit 220 can construct a motion contrast image from the data set acquired by the data acquisition system 130 through such repetitive scans. The motion contrast image is an angiographic image imaged by emphasizing a time course variation of the interference signals caused by the blood flow in the fundus Ef. Typically, OCT angiography is applied to a three dimensional region of the fundus Ef, and an image representing a three dimensional distribution of blood vessels of the fundus Ef is obtained.

When OCT angiography is performed, the image constructing unit 220 can construct any kind of two dimensional angiographic image data and/or any kind of pseudo three dimensional angiographic image data from three dimensional angiographic image data. For example, the image constructing unit 220 can construct two dimensional angiographic image data representing an arbitrary cross section of the fundus Ef by applying multi planar reconstruction to three dimensional angiographic image data.

The image constructing unit 220 is implemented by the cooperation of hardware including a processor and image construction software.

<Data Processor 230>

The data processor 230 includes a processor, and applies various kinds of data processing to an image of the subject's eye E. For example, the data processor 230 is implemented by the cooperation of hardware including a processor and data processing software.

The data processor 230 can perform position matching (i.e., registration) between two images acquired for the fundus Ef. For example, the data processor 230 can perform registration between three dimensional image data acquired by OCT and a front image acquired by the fundus camera unit 2. Further, the data processor 230 can perform registration between two OCT images acquired by OCT. Furthermore, the data processor 230 can perform registration between two front images acquired by the fundus camera unit 2. In addition to this, registration can be applied to an analysis result of an OCT image and/or an analysis result of a front image. The registration can be performed by any known method or technique, and includes, for example, feature point extraction and an affine transformation.

As illustrated in FIG. 4, the data processor 230 of the present embodiment example includes the parameter setting processor 231 and the movement detecting processor 232.

<Parameter Setting Processor 231>

The parameter setting processor 231 sets a focus control parameter based on an OCT image of the fundus Ef acquired in advance. This OCT image (referred to as a preparatory image) is used for rough detection of the shape of an application area of a wide angle OCT scan, and the focus control parameter may be set based on the shape detected.

The ophthalmic imaging apparatus 1 is capable of acquiring an OCT image used for setting of a focus control parameter. For example, the ophthalmic imaging apparatus 1 may apply a preparatory OCT scan to the subject's eye E before applying a wide angle OCT scan to the subject's eye E.

A preparatory OCT scan is performed to pass through both a central region and a peripheral region of a wide angle OCT scan application area. For example, when performing a preparatory OCT scan for a wide angle OCT scan of the fundus Ef, the macula region (and a vicinity thereof) may be set as the central region of the fundus Ef, and the region away from the macula by a predetermined distance or more may be set as the peripheral region. On the other hand, when performing a preparatory OCT scan for a wide angle OCT scan of the anterior eye segment, the corneal apex and its vicinity may be set as the central region of the anterior eye segment, and the region away from the corneal apex by a predetermined distance or more may be set as the peripheral region. More generally, the ocular axis of the subject's eye E and its vicinity may be set as the central region, and the region away from the ocular axis by a predetermined distance or more may be set as the peripheral region.

The pattern of a preparatory OCT scan may be a scan pattern that includes a large number of scan points such as a three dimensional scan (raster scan). However, considering that the purpose of a preparatory OCT scan is rough detection of the shape of a wide angle OCT scan application area (detection of an approximate shape of a wide angle OCT scan application area), a relatively simple scan pattern, such as a B-scan (line scan), a cross scan, or a radial scan, suffices.

The image constructing unit 220 constructs a preparatory image from data acquired by the preparatory OCT scan. The preparatory image typically includes one or more B-scan images that represent both one or more cross sections of the central region and one or more cross sections of the peripheral region of the wide angle OCT scan application area.

In the following examples, the outer edge of the central region and the outer and inner edges of the peripheral region are all circular shapes; however, the shape of the central region and the shape of the peripheral region are not limited thereto. For example, any one or more of the outer edge of a central region and the outer and the inner edges of a peripheral region may be rectangular, or may be any shape. Further, the outer edge shape and the inner edge shape of a peripheral region may be the same as or different from each other.

Figure 5A:
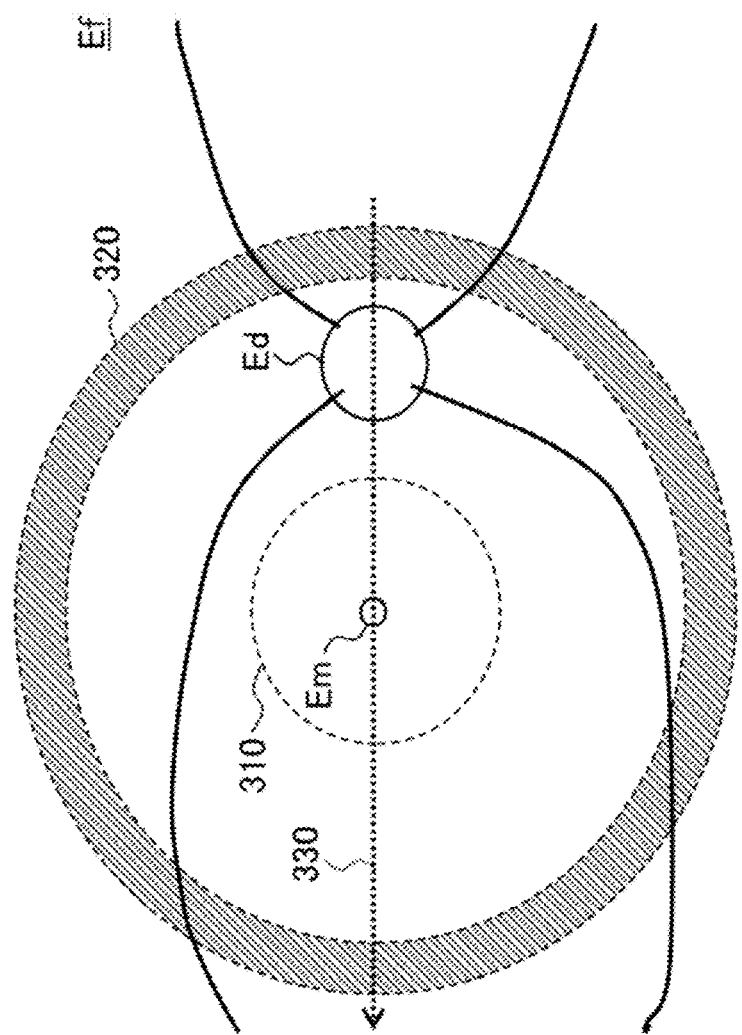
FIG. 5A is a schematic diagram for describing an example of processing performed by the ophthalmic imaging apparatus according to the embodiment example.

FIG. 5A shows an example of a preparatory OCT scan. The preparatory OCT scan of the present example consists of a single B-scan (B-scan 330). The B-scan 330 passes through both the central region 310 and the peripheral region 320. The central region 310 includes the macula Em of the fundus Ef, and the peripheral region 320 is the region represented by hatching and is located away from the macula Em. The reference character "Ed" denotes the optic nerve head. The present example applies the B-scan 330 to a cross section, and then constructs a single B-scan image representing the cross section. The B-scan image of the present example represents a relative relationship between the depth position (z position, z coordinate) of the central region 310 and the depth position of the peripheral region 320. The present example obtains a relative depth position relationship between the central region 310 and the peripheral region 320 only for the direction in which the B-scan 330 is performed.

Figure 5B:
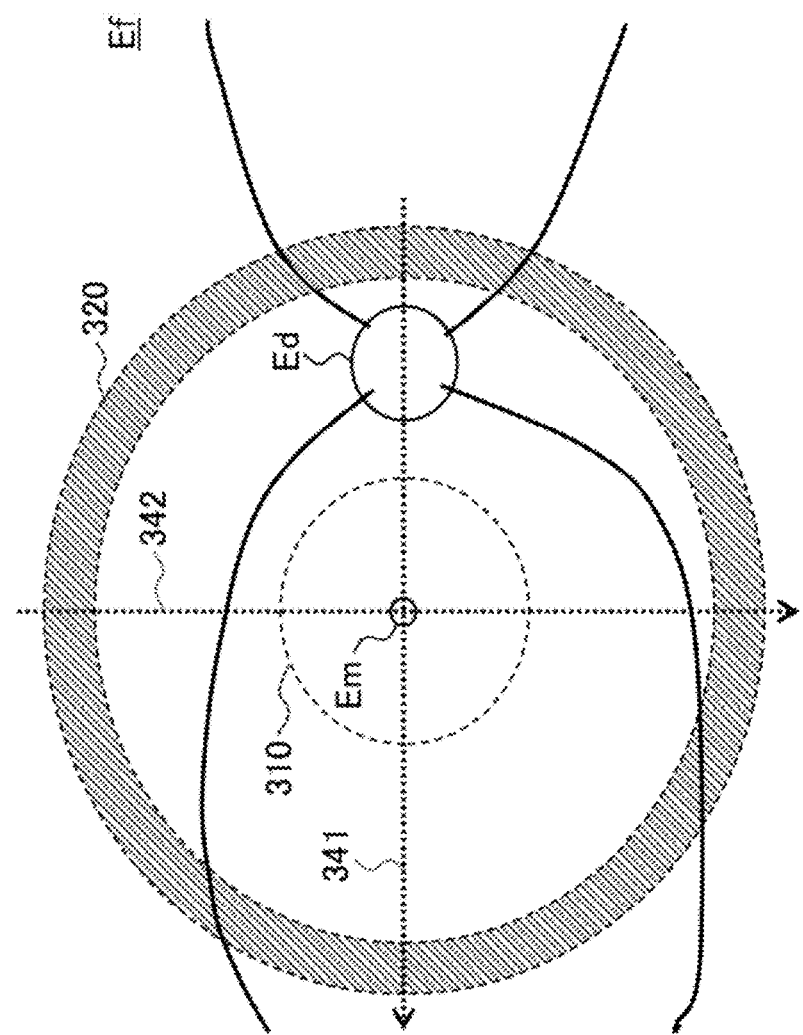
FIG. 5B is a schematic diagram for describing an example of processing performed by the ophthalmic imaging apparatus according to the embodiment example.

FIG. 5B shows another example of a preparatory OCT scan. The preparatory OCT scan of the present example consists of two B-scans (the B-scan 341 and the B-scan 342). The B-scan 341 and the B-scan 342 each pass through both the central region 310 and the peripheral region 320. The two B-scans 341 and 342 are orthogonal to each other. In other words, the preparatory OCT scan of the present example is a cross scan. The present example obtains a B-scan image representing a cross section to which the B-scan 341 is applied and another B-scan image representing a cross section to which the B-scan 342 is applied. Each of the two B-scan images of the present example represents a relative relationship between the depth position (z position, z coordinate) of the central region 310 and the depth position of the peripheral region 320. The present example obtains a relative depth position relationship between the central region 310 and the peripheral region 320 for each of the direction in which the B-scan 341 is performed and the direction in which the B-scan 342 is performed, that is, for two directions e orthogonal to each other.

Although not shown in the drawings, when a radial scan, which consists of a plurality of B-scans arranged at equal angular intervals, is employed as a preparatory OCT scan, a relative depth position relationship between a central region and a peripheral region may be obtained for each of the corresponding plurality of directions arranged at equal angular intervals. Also, although not shown in the drawings, when a three dimensional scan (e.g., a raster scan) is used as a preparatory OCT scan, a relative depth position relationship between a central region and a peripheral region may be obtained for each of any one or more directions in the xy plane. Also in the cases where other scan patterns are employed as a preparatory OCT scan, a relative depth position relationship between a central region and a peripheral region may be obtained for each of one or more directions according to a scan pattern employed.

In this way, the pattern of a preparatory OCT scan determines the content or quality (e.g., direction) of information and/or the amount or quantity (e.g., angular interval) of information to be acquired as a relative depth position relationship(s). Conversely, the pattern of a preparatory OCT scan may be determined based on the content (quality) and/or the amount (quantity) of information designed to be acquired as a relative depth position relationship(s). The determination of a preparatory OCT scan pattern may be made, for example, in advance or for each examination.

Data acquired by a preparatory OCT scan is sent to the image constructing unit 220, and a preparatory image is then constructed therefrom. The parameter setting processor 231 performs setting of one or more focus control parameters based on the preparatory image constructed. As described above, the focus control parameter is a parameter indicating the content of control for the OCT focus driver 43A, and examples of the focus control parameter include a parameter indicating the focal position of the measurement arm, a parameter indicating the moving speed (velocity) of the focal position, and a parameter indicating the acceleration in the movement of the focal position.

Figure 6A:
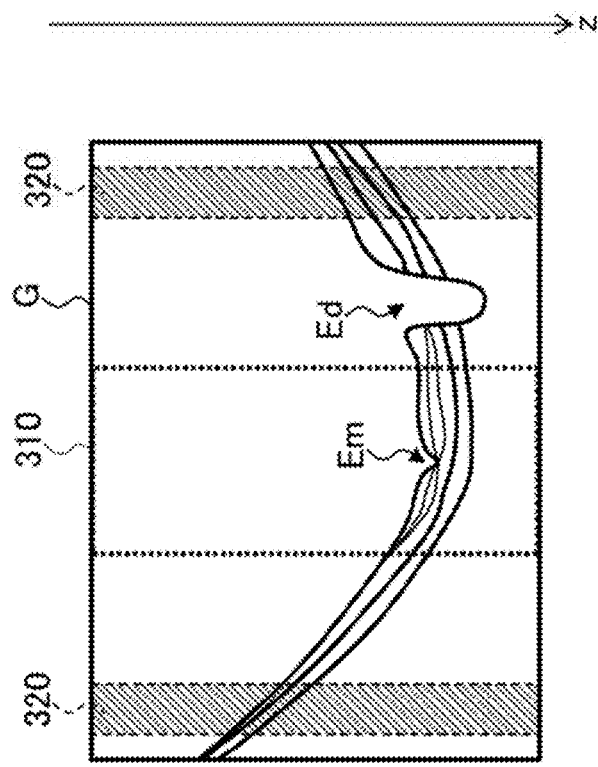
FIG. 6A is a schematic diagram for describing an example of processing performed by the ophthalmic imaging apparatus according to the embodiment example.

An example of the process executed by the parameter setting processor 231 will be described. FIG. 6A shows an example of a preparatory image. The preparatory image G is, for example, an image constructed from data acquired by the B-scan 330 shown in FIG. 5A (or, by the B-scan 341 shown in FIG. 5B or by a B-scan similar thereto). The region defined by the dotted line and denoted by the reference character "310" corresponds to the intersection region (common region) between the central region 310 and the B-scan 330 shown in FIG. 5A. The regions represented by hatching and denoted by the reference character "320" correspond to the intersection regions (common regions) between the peripheral region 320 and the B-scan 330 shown in FIG. 5A. It should be noted that the preparatory image G has two peripheral regions 320. The reference character "Em" denotes an image region of the macula, and the reference character "Ed" denotes an image region of the optic nerve head.

The parameter setting processor 231 analyzes the central region 310 of the preparatory image G to detect the macula region Em, and then determines the depth position (z coordinate) of the macula region Em. For the macula region detection and the depth position determination, the parameter setting processor 231 may execute processing including the following processes, for example: segmentation to identify an image region of the inner limiting membrane (ILM); shape analysis to detect the macula region Em based on the shape (small hollow) of the inner limiting membrane region identified; and determination of the z coordinate of a pixel corresponding to a representative point in the macula region Em detected. The representative point in the macula region Em may be, for example, the macular center (fovea centralis, the deepest part of the hollow). The z coordinate of the macular center obtained by the present example will be denoted by the reference character "$z_1$" (see FIG. 6B). Note that the site for which the z coordinate is determined is not limited to the macular center, and may be any representative point within the central region 310.

Further, the parameter setting processor 231 analyzes the peripheral region 320 of the preparatory image G to detect an image region of a predetermined tissue (e.g., the inner limiting membrane), and then determines the depth position (z coordinate) of the image region detected. For the image region detection and the depth position determination, the parameter setting processor 231 executes processing including, for example, segmentation to identify an image region of the predetermined tissue and determination of the z coordinate of a pixel corresponding to a representative point in the image region detected. The representative point in the image region of the predetermined tissue may be, for example, the center position of the peripheral region 320 in the B-scan direction, or a position on the edge of the peripheral region 320. The z coordinates of the inner limiting membrane obtained by the present example in the case where the two center positions of the two peripheral regions 320 of the preparatory image G are the representative points, will be denoted by the reference characters "$z_{21}$" and "$z_{22}$" (see FIG. 6C).

Further, the parameter setting processor 231 sets the focus control parameter based on the z coordinate ($z_1$) of the representative point of the central region 310 and the z coordinates ($z_{21}$ and $z_{22}$) of the representative points of the peripheral region 320.

For example, the parameter setting processor 231 may determine the position of the OCT focusing lens 43 corresponding to the z coordinate ($z_1$) of the representative point in the central region 310, and also determine the positions of the OCT focusing lens 43 respectively corresponding to the z coordinates ($z_{21}$ and $z_{22}$) of the representative points in the peripheral region 320. A position of the OCT focusing lens 43 corresponds to a focal position of the measurement arm. The present example may be described as a process of finding absolute positions of the OCT focusing lens 43. The processing of the present example is performed based on, for example, the coherence gate position (e.g., the arm length, the position of the retroreflector 41, the position of the retroreflector 114) at the time point of the acquisition of the preparatory image G, and on the scale of the z-axis (e.g., distance per pixel).

The parameter setting processor 231 may calculate the difference between the position (focal position) of the OCT focusing lens 43 corresponding to the z coordinate ($z_1$) of the representative point of the central region 310 and the positions (focal positions) of the OCT focusing lens 43 respectively corresponding to the z coordinates ($z_{21}$ and $z_{22}$) of the representative points of the peripheral region 320. In other words, the present example may be said to be a process of determining relative positions of the OCT focusing lens 43. The processing of the present example is performed based on the scale of the z-axis, for example.

The parameter setting processor 231 may determine a focal position change range that includes both the position (focal position) of the OCT focusing lens 43 corresponding to the z coordinate ($z_1$) of the representative point of the central region 310 and the positions (focal positions) of the OCT focusing lens 43 respectively corresponding to the z coordinates ($z_{21}$ and $z_{22}$) of the representative points of the peripheral region 320. The focal position change range is a range of the focal position changed by the focus control, and is defined as a range in which the OCT focusing lens 43 is moved, for example. The processing of the present example is executed based on, for example, the coherence gate position at the time point of the acquisition of the preparatory image G, and on the scale of the z-axis.

The parameter setting processor 231 may set the speed at which the focal position of the measurement arm is moved. The processing of the present example is executed based on the absolute position or the relative position of the OCT focusing lens 43 described above, or based on the movement range of the OCT focusing lens 43, for example.

The parameter setting processor 231 may set the acceleration at which the focal position of the measurement arm is moved. The processing of the present example is executed based on the absolute position or the relative position of the OCT focusing lens 43, or based on the movement range of the OCT focusing lens 43, for example. Alternatively, the processing is executed based on the movement speed of the OCT focusing lens 43.

Figure 7:
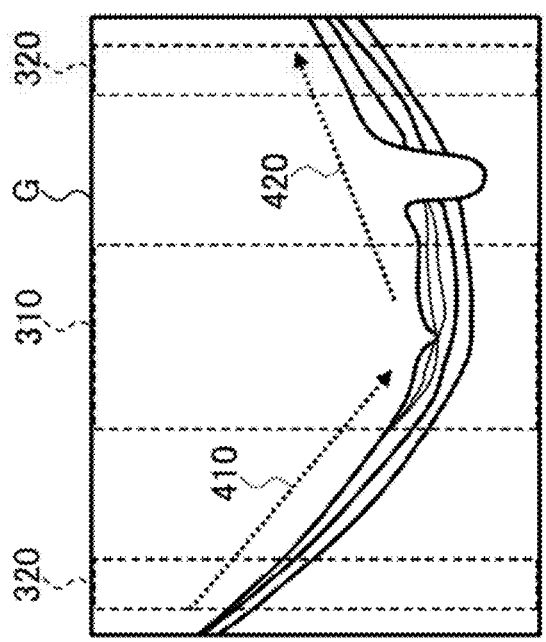
FIG. 7 is a schematic diagram for describing an example of processing performed by the ophthalmic imaging apparatus according to the embodiment example.

When the preparatory image G is obtained, the parameter setting processor 231 sets the focus control parameter, for example, as shown in FIG. 7, such that the focal position moves in the +z direction as it moves from the left peripheral region 320 side toward the central region 310 side, and also such that the focal position moves in the −z direction as it moves from the central region 310 side toward the right peripheral region 320 side.

The parameter setting processor 231 may generate information that represents the relationship between the scan control parameter and the focus control parameter based on any of the examples of the focus control parameter mentioned above, for example.

Prior to the information generation, a scan pattern for wide angle OCT scanning is set. The setting of the wide angle OCT scan pattern may be performed in advance or for each examination, for example.

In the present embodiment example, the wide angle OCT scan pattern includes the first partial pattern and the second partial pattern. The first partial pattern is a continuous pattern applied to the central region of the wide angle OCT scan application area, and the second partial pattern is a continuous pattern applied to the peripheral region of the wide angle OCT scan application area. The first partial pattern is a scan pattern for continuously scanning at least a part of the central region, and the second partial pattern is a scan pattern for continuously scanning at least a part of the peripheral region. Here, "continuously scanning" means, for example, scanning a plurality of scan points arranged in a predetermined pattern sequentially according to the arrangement order of the scan points.

The wide angle OCT scan pattern may include a curved scan pattern defined in a polar coordinate system whose origin is located at the center of the wide angle OCT scan application area. The center of the wide angle OCT scan application area may be, for example, the macular center, or may be another site of the eye fundus. In this way, the center of the wide angle OCT scan application area may be defined on the basis of the site or tissue of the subject's eye. However, the center of the wide angle OCT scan application area may also be defined on the basis of the ophthalmic imaging apparatus 1. For example, the center of the wide angle OCT scan application area may be defined as the neutral position (neutral orientation) of the orientation variable mirror (e.g., galvano mirror) of the optical scanner 44, or as the position of the optical axis of the measurement arm (e.g., the optical axis of the objective lens 22). Examples of a wide angle OCT scan pattern of a curved shape defined by a polar coordinate system whose origin is located at the center of a wide angle OCT scan application area, include a spiral scan pattern and a concentric circular scan pattern.

Figure 8A:
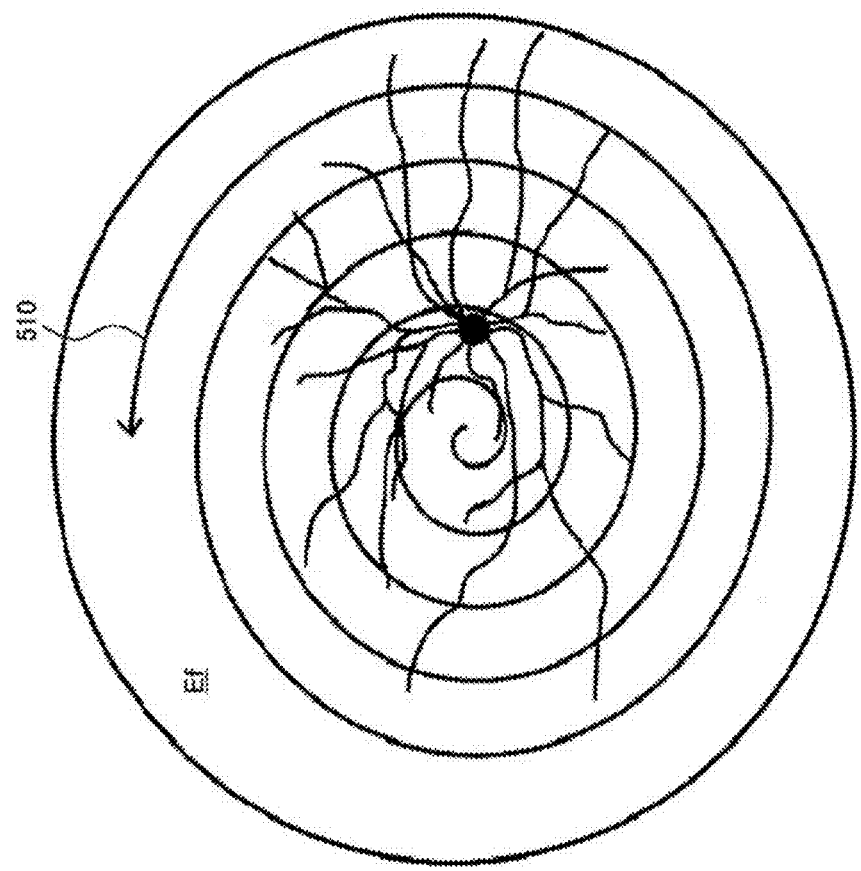
FIG. 8A is a schematic diagram for describing an example of processing performed by the ophthalmic imaging apparatus according to the embodiment example.
Figure 8B:
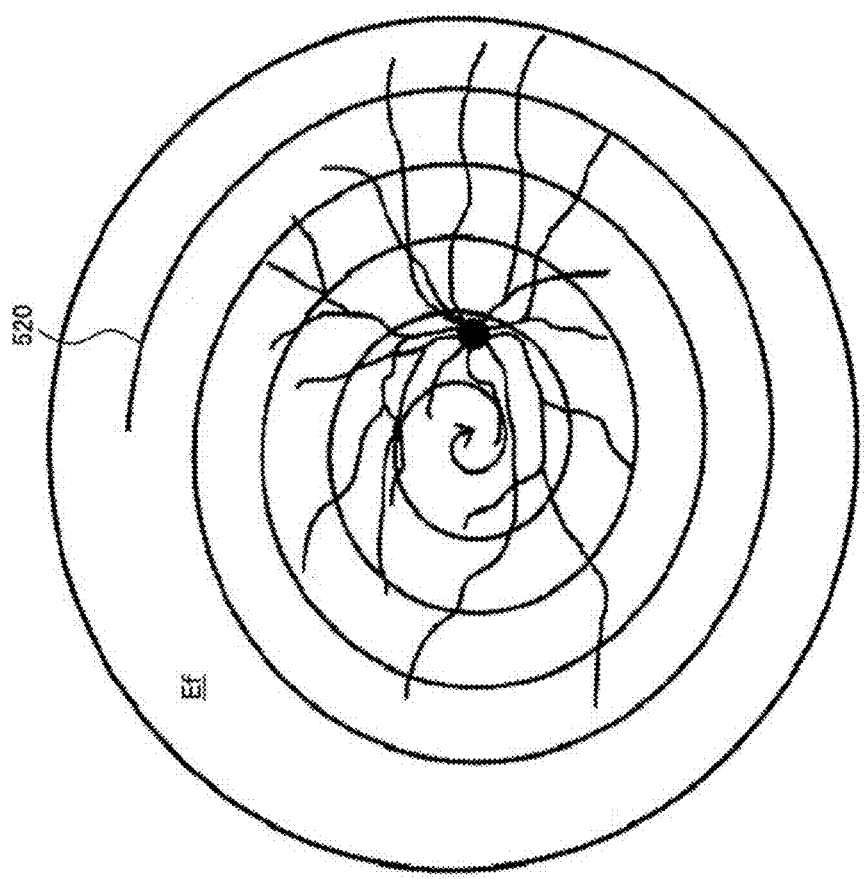
FIG. 8B is a schematic diagram for describing an example of processing performed by the ophthalmic imaging apparatus according to the embodiment example.

In the case where the wide angle OCT scan pattern is the curved scan pattern described above, the wide angle OCT scan pattern may be a spiral scan pattern directed from the center to the outer edge of the wide angle OCT scan application area (see the spiral scan pattern 510 shown in FIG. 8A), or may be a spiral scan pattern directed from the outer edge to the center of the wide angle OCT scan application area (see the spiral scan pattern 520 shown in FIG. 8B).

The spiral scan pattern 510 shown in FIG. 8A has the macular center within the central region (not shown in the drawing) as a scan start point, passes through the peripheral region (not shown in the drawing) while increasing the radial distance (radial coordinate, radius) as the polar angle (polar coordinate, azimuth) changes, and reaches a scan end point located on the outer edge (or located in a vicinity area thereof).

The spiral scan pattern 520 shown in FIG. 8B has a position on the outer edge (or a position in a vicinity area thereof) as a scan start point, passes through the peripheral region (not shown in the drawing) while decreasing the radial distance as the polar angle changes, and reaches a scan end point that is the macular center within the central region (not shown in the drawing).

The space of the spiral trajectory (locus) of each of the spiral scan pattern 510 is represented larger (coarser) than the actual space for the sake of illustration. The same applies to the spiral scan pattern 520. In reality, for example, the space of each spiral may be smaller (denser) to the extent that three dimensional image data can be constructed based thereon.

Some examples of the focus control parameter that can be set by the parameter setting processor 231 in the case where the wide angle OCT scan pattern is the above-mentioned curved scan pattern (e.g., the spiral scan pattern), will be described with reference to FIG. 9A to FIG. 9D.

It should be noted that the focus control parameter that can be set by the parameter setting processor 231 is not limited to these examples, and may be any focus kinds of control parameters that satisfy the conditions required in the present embodiment example.

Figure 9A:
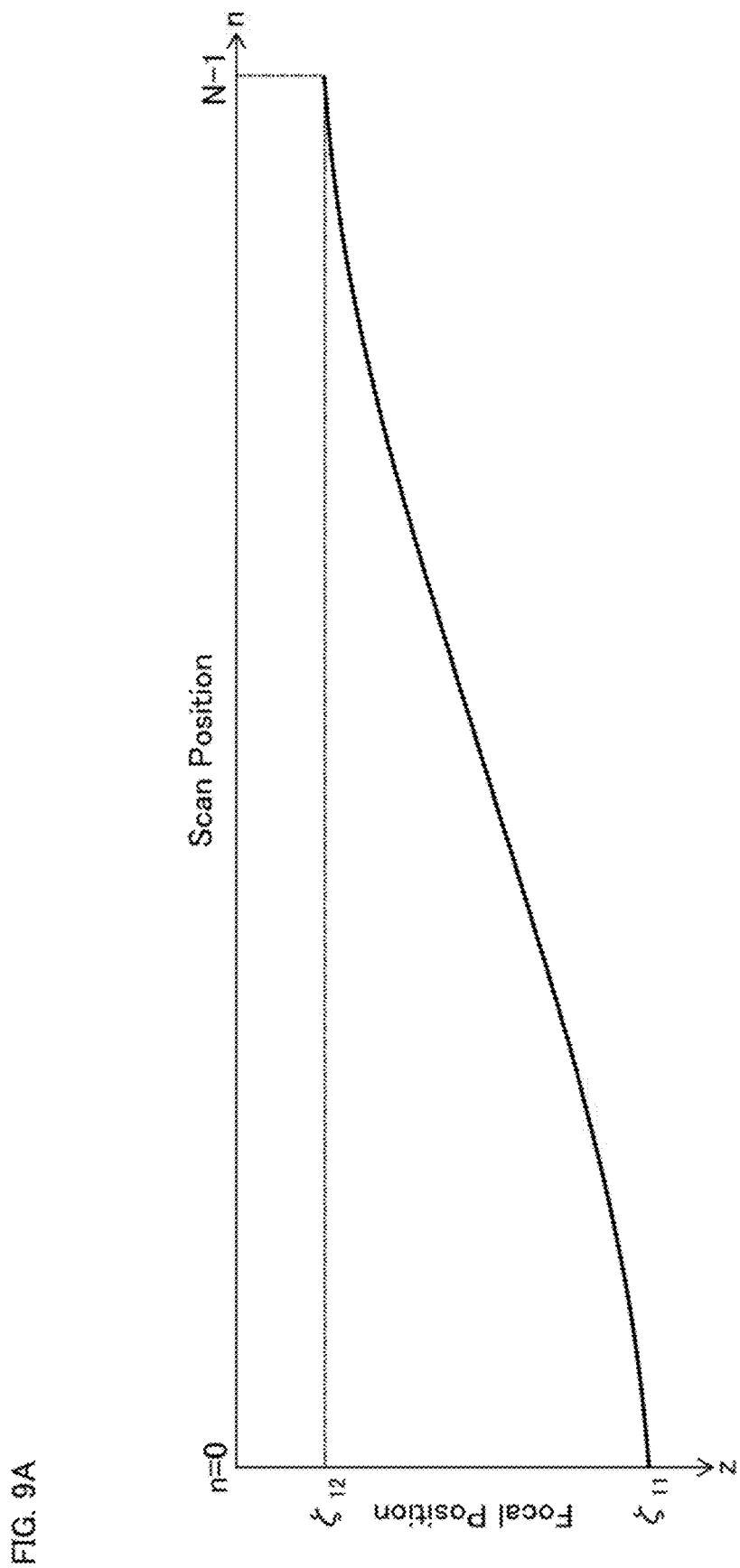
FIG. 9A is a schematic diagram for describing an example of processing performed by the ophthalmic imaging apparatus according to the embodiment example.

In the example shown in FIG. 9A, the horizontal axis of the coordinate system indicates the scan position, and the vertical axis indicates the focal position. The scan positions on the horizontal axis are defined as the number n (n=0, 1, 2, ..., N−1) of N scan points ordered according to the scan pattern to be applied. The focal positions on the vertical axis are defined as the z coordinates. The focus control parameter of FIG. 9A may be applied in the case of employing a spiral scan pattern directed from the center to the outer edge of a wide angle OCT scan application area, such as the spiral scan pattern 510 shown in FIG. 8A, for example. Below, a description will be given along with the spiral scan pattern 510 as an example.

The first scan position n=0 in FIG. 9A corresponds to the scan start point (macular center) in the spiral scan pattern 510, and the last scan position n=N−1 corresponds to the scan end point (a position on the outer edge, or a position in a vicinity of the outer edge) in the spiral scan pattern 510.

Figure 6B:
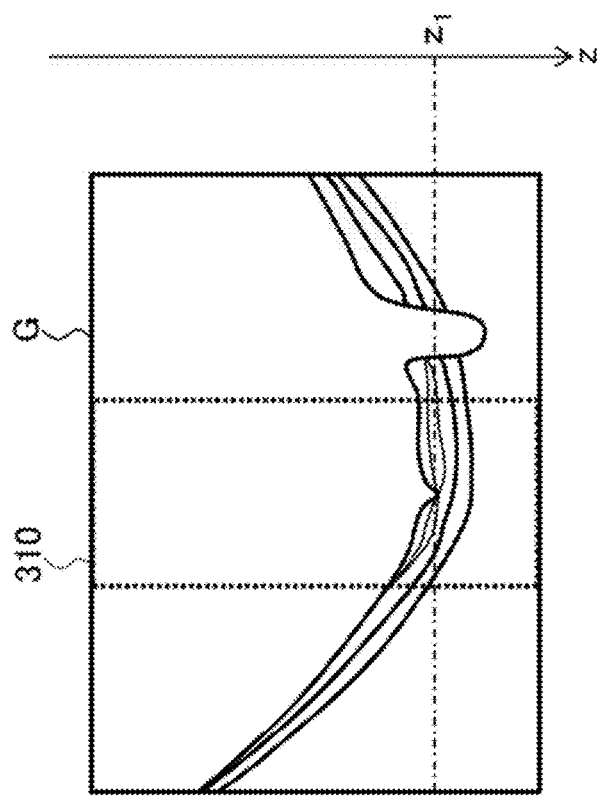
FIG. 6B is a schematic diagram for describing an example of processing performed by the ophthalmic imaging apparatus according to the embodiment example.

The focal position $\zeta_{11}$ assigned to the scan start position n=0 may be determined based on the z coordinate $z_1$ of the central region 310 (e.g., the macular center) shown in FIG. 6B, for example. For example, $\zeta_{11}$ is set to be equal to $z_1$, or $\zeta_{11}$ is set to a value approximately equal to $z_1$.

Figure 6C:
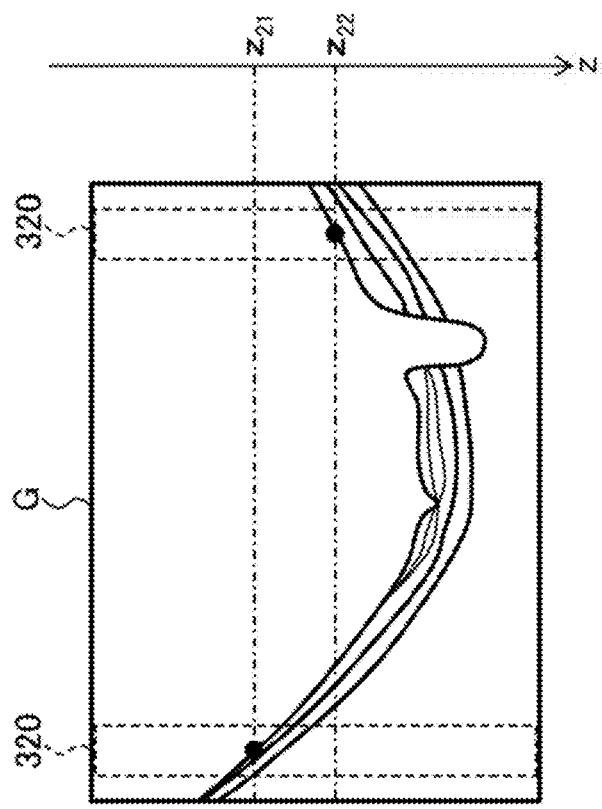
FIG. 6C is a schematic diagram for describing an example of processing performed by the ophthalmic imaging apparatus according to the embodiment example.

The focal position $\zeta_{12}$ assigned to the scan end position n=N−1 is determined based on at least one of the z coordinates $z_{21}$ and $z_{22}$ of the peripheral region 320 shown in FIG. 6C, for example. In some examples, $\zeta_{12}$ is set to be equal to $z_{21}$, $\zeta_{12}$ is set to a value approximately equal to $z_{21}$, $\zeta_{12}$ is set to be equal to $z_{22}$, $\zeta_{12}$ is set to a value approximately equal to $z_{22}$, or $\zeta_{12}$ is set to a value determined based on both $z_{21}$ and $z_{22}$. Any statistical processing may be used to determine from both $z_{21}$ and $z_{22}$. Examples of the statistical processing include the following: a process of calculating the average of $z_{21}$ and $z_{22}$; a process of calculating a weighted average of $z_{21}$ and $z_{22}$; and a process of selecting the greater value or the lesser value of $z_{21}$ and $z_{22}$.

The focus control parameter shown in FIG. 9A may be set as a smooth curve (e.g., a spline curve, a Bézier curve) that connects the coordinates (0, $\zeta_{11}$) corresponding to the scan start point and the coordinates (N−1, $\zeta_{12}$) corresponding to the scan end point in the two dimensional coordinate system (n, z).

Figure 9B:
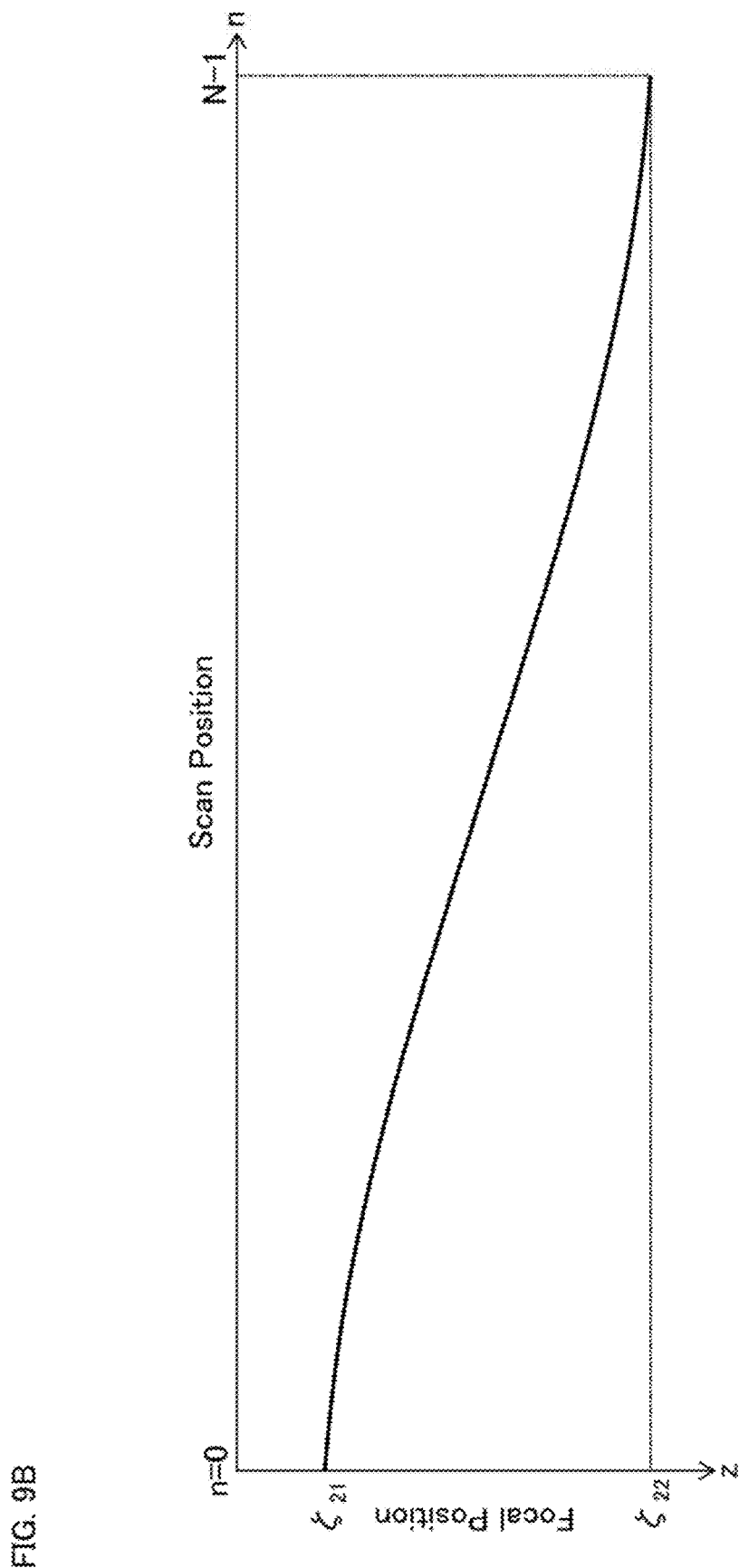
FIG. 9B is a schematic diagram for describing an example of processing performed by the ophthalmic imaging apparatus according to the embodiment example.

The two dimensional coordinate system (n, z) in the example shown in FIG. 9B is the same as that in the example shown in FIG. 9A. The focus control parameter of FIG. 9B is applicable when a spiral scan pattern directed from the outer edge to the center of a wide angle OCT scan application area is employed, such as the spiral scan pattern 520 shown in FIG. 8B, for example. Below, a description will be given along with the spiral scan pattern 520 as an example.

The first scan position n=0 in FIG. 9B corresponds to the scan start point (a position on the outer edge, or a position in a vicinity of the outer edge) in the spiral scan pattern 520, and the last scan position n=N−1 corresponds to the scan end point (macular center) in the spiral scan pattern 520.

The focal position $\zeta_{21}$ assigned to the scan start position n=0 may be determined in the same manner as the focal position $\zeta_{12}$ in FIG. 9A, for example. Further, the focal position $\zeta_{22}$ assigned to the scan end position n=N−1 may be determined in the same manner as the focal position $\zeta_{11}$ in FIG. 9A, for example.

The focus control parameter shown in FIG. 9B may be set as a smooth curve (e.g., a spline curve, a Bézier curve) that connects the coordinates (0, $\zeta_{21}$) corresponding to the scan start point and the coordinates (N−1, $\zeta_{22}$) corresponding to the scan end point in the two dimensional coordinate system (n, z).

Figure 9C:
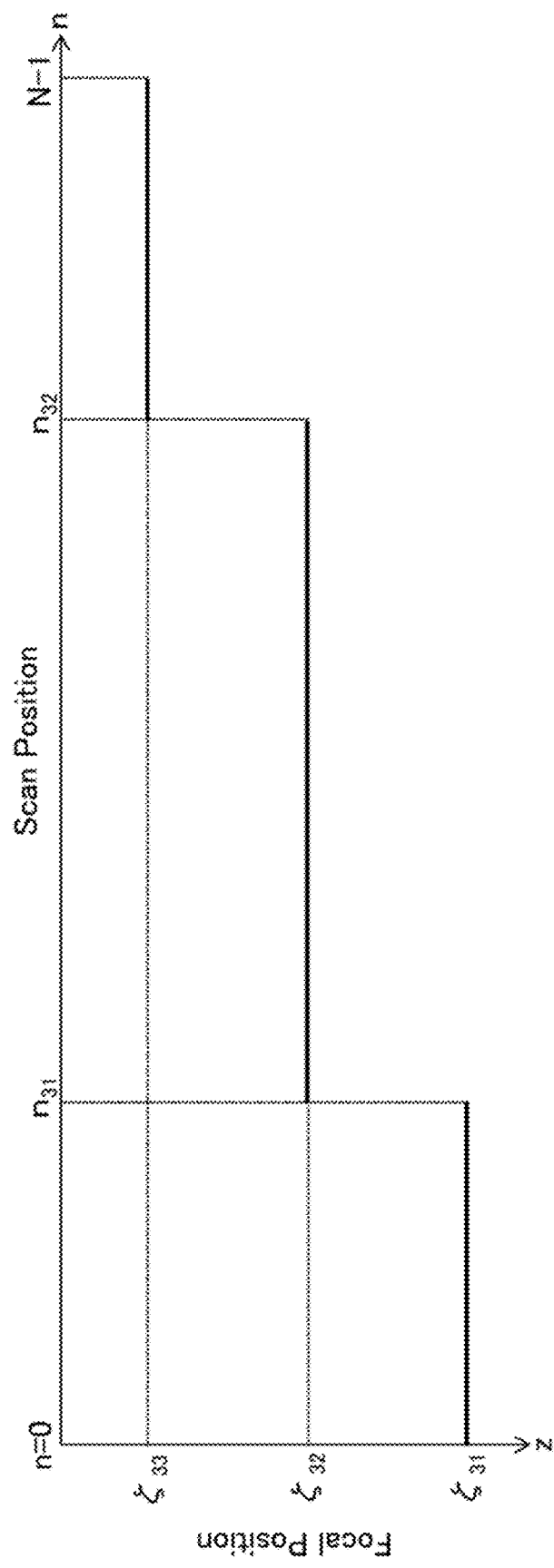
FIG. 9C is a schematic diagram for describing an example of processing performed by the ophthalmic imaging apparatus according to the embodiment example.

The two dimensional coordinate system (n, z) in the example shown in FIG. 9C is the same as that in the example shown in FIG. 9A. The focus control parameter of FIG. 9C is applicable when a spiral scan pattern directed from the center to the outer edge of a wide angle OCT scan application area is employed, such as the spiral scan pattern 510 shown in FIG. 8A, for example. Below, a description will be given along with the spiral scan pattern 510 as an example.

The first scan position n=0 in FIG. 9C corresponds to the scan start point (macular center) in the spiral scan pattern 510, and the last scan position n=N−1 corresponds to the scan end point (a position on the outer edge, or a position in a vicinity of the outer edge) in the spiral scan pattern 510.

The focal position $\zeta_{31}$ assigned to the section n=[0, $n_{31}$] of the scan position may be determined in the same manner as the focal position $\zeta_{11}$ in FIG. 9A, for example. Further, the focal position $\zeta_{33}$ assigned to the section n=[$n_{32}$, N−1] of the scan position may be determined in the same manner as the focal position $\zeta_{12}$ in FIG. 9A, for example. In addition, the focal position $\zeta_{32}$ assigned to the section n=($n_{31}$, $n_{32}$)=[$n_{31}$+1, $n_{32}$−1] of the scan position may be determined based on, for example, the focal positions $\zeta_{31}$ and $\zeta_{33}$. Typically, the focal position $\zeta_{32}$ is determined by, for example, any statistical processing. Examples of the statistical values thus determined include the following: the average of $\zeta 31$ and $\zeta_{33}$; a weighted average of $\zeta_{31}$ and $\zeta_{33}$; the greater value of $\zeta_{31}$ and $\zeta_{33}$; and the lesser value of $\zeta_{31}$ and $\zeta_{33}$.

Similar to the relationship between the focus control parameter shown in FIG. 9A and the focus control parameter shown in FIG. 9B, the focus control parameter of a stepwise shape shown in FIG. 9C may be inverted. The focus control parameter obtained by inversion is applicable when a spiral scan pattern directed from the outer edge to the center of a wide angle OCT scan application area is employed, such as the spiral scan pattern 520 shown in FIG. 8B, for example.

Furthermore, a modification may be applied to the focus control parameter shown in FIG. 9C. For example, a smooth curve (e.g., a spline curve, a Bézier curve) that connects the coordinates $(0, \zeta_{31})$ and the coordinates $(n_{31}, \zeta_{32})$ may be assigned to the section $n=[0, n_{31}]$ of the scan position. In addition, a smooth curve (e.g., a spline curve, a Bézier curve) that connects the coordinates $(n_{32}, \zeta_{32})$ and the coordinates $(N-1, \zeta_{33})$ may be assigned to the section $n=[n_{32}, N-1]$ of the scan position. For example, when a spiral scan pattern directed from the outer edge to the center of a wide angle OCT scan application area is employed, such as the spiral scan pattern 520 shown in FIG. 8B, it is possible to invert the focus control parameter a part of which is replaced by a curve.

As an alternative, the straight line (the sloping line) that connects the coordinates $(0, \zeta_{31})$ and the coordinates $(n_{31}, \zeta_{32})$ may be assigned to the section $n=[0, n_{31}]$ of the scan position. In addition, the straight line (the sloping line) that connects the coordinates $(n_{32}, \zeta_{32})$ and the coordinates $(N-1, \zeta_{33})$ may be assigned to the section $n=[n_{32}, N-1]$ of the scan position. For example, when a spiral scan pattern directed from the outer edge to the center of a wide angle OCT scan application area is employed, such as the spiral scan pattern 520 shown in FIG. 8B, it is possible to invert the focus control parameter a part of which is replaced by a sloping line.

Figure 9D:
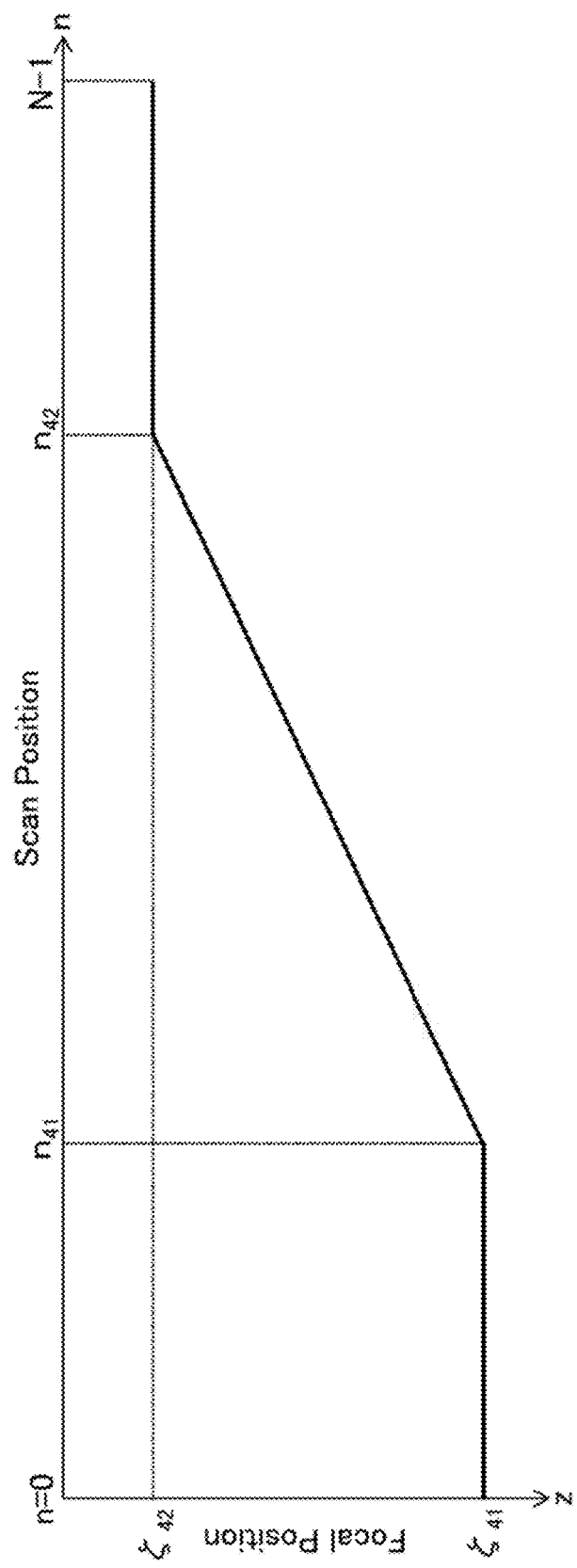
FIG. 9D is a schematic diagram for describing an example of processing performed by the ophthalmic imaging apparatus according to the embodiment example.

The two dimensional coordinate system (n, z) in the example shown in FIG. 9D is the same as that in the example shown in FIG. 9A. The focus control parameter of FIG. 9D is applicable when a spiral scan pattern directed from the center to the outer edge of a wide angle OCT scan application area is employed, such as the spiral scan pattern 510 shown in FIG. 8A, for example. Below, a description will be given along with the spiral scan pattern 510 as an example.

The first scan position $n=0$ in FIG. 9D corresponds to the scan start point (macular center) in the spiral scan pattern 510, and the last scan position $n=N-1$ corresponds to the scan end point (a position on the outer edge, or a position in a vicinity of the outer edge) in the spiral scan pattern 510.

The focal position 41 assigned to the section $n=[0, n_{41}]$ of the scan position may be determined in the same manner as the focal position $\zeta_{11}$ in FIG. 9A, for example. Further, the focal position $\zeta_{42}$ assigned to the section $n=[n_{42}, N-1]$ of the scan position may be determined in the same manner as the focal position $\zeta_{12}$ in FIG. 9A, for example. In addition, the straight line that connects the coordinates $(n_{41}, \zeta_{41})$ and the coordinates $(n_{42}, \zeta_{42})$ is assigned to the section $n=(n_{41}, n_{42})=[n_{41}+1, n_{42}-1]$ of the scan position.

Similar to the relationship between the focus control parameter shown in FIG. 9A and the focus control parameter shown in FIG. 9B, the focus control parameter shown in FIG. 9D may be inverted. The focus control parameter obtained by inversion is applicable when a spiral scan pattern directed from the outer edge to the center of a wide angle OCT scan application area is employed, such as the spiral scan pattern 520 shown in FIG. 8B, for example.

Furthermore, a modification may be applied to the focus control parameter shown in FIG. 9D. For example, a smooth curve (e.g., a spline curve, a Bézier curve) that connects the coordinates $(n_{41}, \zeta_{41})$ and the coordinates $(n_{42}, \zeta_{42})$ may be assigned to the section $n=(n_{41}, n_{42})=[n_{41}+1, n_{42}-1]$ of the scan position. For example, when a spiral scan pattern directed from the outer edge to the center of a wide angle OCT scan application area is employed, such as the spiral scan pattern 520 shown in FIG. 8B, it is possible to invert the focus control parameter a part of which is replaced by a curve.

While some examples of the processing executed by the parameter setting processor 231 and some examples of the focus control parameters created by that processing have been described above, these examples are not intended to be limiting and hence various kinds of modifications are allowed.

For example, in the example shown in FIG. 6B, the depth position (z coordinate) of a single representative point (macular center) in the central region 310 is determined and used as the depth position of the central region 310. On the other hand, it is possible to determine the respective depth positions of two or more points in the central region, and to determine the depth position of the central region from the two or more depth positions determined. For example, statistical processing may be applied to the two or more depth positions to determine the depth position of the central region. The statistical value obtained from the two or more depth positions may be, for example, any of the average value, a weighted average value, the median, the mode, the maximum value, and the minimum value. The same processing may be applied to determination of the depth position of the peripheral region.

In the case of determining two or more depth positions in the central region, information representing the change in depth position within the central region may be obtained from the two or more depth positions, instead of calculating a single statistical value from the two or more depth positions and using the calculated statistical value as the depth position of the central region as described above. For example, based on the two or more depth positions, a graph representing a curvilinear, linear, or stepwise change in the depth position in the central region (focus control parameter) can be obtained. FIG. 9A and FIG. 9B are examples of the curvilinear change. As an example of the linear change in the depth position in the central region, it is possible to obtain a straight line that connects the coordinates $(0, \zeta_{31})$ and the coordinates $(n_{31}, \zeta_{32})$ in the two dimensional coordinate system shown in FIG. 9C, although not shown in the drawings. Further, as an example of the stepwise change in the depth position in the central region, it is possible to set a focus control parameter in the section $n=[0, n_{31}]$ of the scan position, whose values of the focal position change in a stepwise manner from $\zeta_{31}$ to $\zeta_{32}$ in the two dimensional coordinate system shown in FIG. 9C, although not shown in the drawings. The same processing may be applied in the case of determining the focus control parameter for the peripheral region.

As described above, the process of setting the focus control parameter by determining two or more depth positions in the center region is considered to be effective, for example, in the following cases: where the width of the central region (the length of the central region in a certain direction orthogonal to the z direction) is relatively wide; and where the depth position in the central region varies relatively greatly (e.g., where the difference between the maximum depth position and the minimum depth position in the central region is relatively large). The parameter setting processor 231 may be configured to determine the number (and positions) of points in the central region where the depth region is to be determined, according to the size of the width of the central region and/or according to the magnitude of the change in the depth position within the central region. The same processing may also be applied to the case of determining the focus control parameter for the peripheral region.

In the examples described above, the central region (310) and the peripheral region (320) are apart from each other. In other words, there is an annular intermediate region between the outer edge of the central region and the inner edge of the peripheral region in the examples described above. In some other examples, the outer edge of a central region and the inner edge of a peripheral region may be the same.

More generally, the central region and the peripheral region of the present embodiment example may be defined in an arbitrary manner. For example, the central region and the peripheral region may be defined according to a certain site of the fundus. As a specific example, the central region may be set to a region the center of which corresponds to a predetermined site of the fundus (e.g., macular center) and each point of which is located at a predetermined first distance or less away from the center. In addition to this, the peripheral region may be set to a region each point of which is located at a predetermined second distance (the second distance is equal to or longer than the first distance) or more away from the same center. Here, a third distance that defines the outer edge of the peripheral region may be further set, or the outer edge of the peripheral region may be set to the outer edge of the wide angle OCT scan application area. The distance in the present example may be defined by any of a distance in the fundus, an optically calculated distance, and a standard distance obtained from a model eye or clinical data.

Another definition of the central region and the peripheral region is a definition according to OCT scanning. For example, the central region may be set to a predetermined first region in the wide angle OCT scan application area, and the peripheral region may be set to a predetermined second region that is different from the first region. Typically, the central region may be set to the first region that includes the center of the wide angle OCT scan application area, and the peripheral region may be set to the second region located outside the first region.

In the example described above, scan patterns consisting of curves, such as a spiral scan pattern, have been described in particular. However, a scan pattern at least a part of which is a straight line may also be employed in other examples. For example, a spiral-like scan pattern consisting of a plurality of straight lines may be obtained by combining multiple line scans along the x direction and multiple line scans along the y direction in an alternate manner.

The setting of the wide angle OCT scan pattern and the focus control parameters (and also the scan speed) illustrated above includes the setting of the movement speed and/or the movement acceleration of the focal position. For example, in the focus control parameter illustrated in each of FIG. 9A to FIG. 9D, the slope (gradient) of the graph showing the focus control parameter corresponds to the movement speed, and the change rate of the slope of the graph corresponds to the movement acceleration. Conversely, it is possible to perform the setting of the focus control parameter through the setting of the movement speed and/or the movement acceleration of the focal position.

In the focus control parameter illustrated in each of FIG. 9A to FIG. 9D, the focal position applied to the central region (i.e., the first focal position) is located at a position on the +z side than the focal position applied to the peripheral region (i.e., the second focal position). In other words, the focal length corresponding to the first focal position (i.e., the first focal length) is set to be longer than the focal length corresponding to the second focal position (i.e., the second focal length). This processing is designed according to the shape of the subject's eye (the fundus thereof). However, the first focal length does not need to be longer than the second focal length.

The parameter setting processor 231 capable of executing the above processing is implemented by the cooperation of hardware including a processor and parameter setting software.

<Movement Detecting Processor 232>

The ophthalmic imaging apparatus 1 includes the fundus camera unit 2 that performs repetitive photographing of the subject's eye E to acquire a time series image (time course image). The time series image acquired by the fundus camera unit 2 is an observation image mentioned above, for example.

The movement detecting processor 232 analyzes the observation image acquired by the fundus camera unit 2 to detect the movement of the subject's eye E. For example, the movement detecting processor 232 analyzes each image (i.e., each frame) included in the observation image to detect a feature point, and obtains a time course change in the feature point position. The feature point may be the center, the center of gravity, or the contour of the pupil, or may be the center, the center of gravity, or the contour of the iris, for example.

The scan controller 213 can control the optical scanner 44 based on the output from the movement detecting processor 232 while controlling the optical scanner 44 and the OCT unit 100 according to the wide angle OCT scan pattern. The control of the optical scanner 44 on the basis of the output from the movement detecting processor 232 is so-called tracking control.

Tracking is executed by the series of processing, described below, disclosed in, for example, Japanese Unexamined Patent Application Publication No. 2017-153543. To begin with, the movement detecting processor 232 registers, as a reference image, a frame (i.e., a front image) of the observation image acquired by the fundus camera unit 2.

Further, the movement detecting processor 232 determines the change in the position of the feature point in another frame relative to the position of the feature point in the reference image. This process corresponds to determining the time course change in the position of the feature point, that is, determining the positional differences between the reference image and other frames. In the case where the positional difference exceeds a threshold value or the positional difference cannot be detected due to blinking or fixation error, the movement detecting processor 232 may register a frame acquired thereafter as a new reference image. Further, the method or technique of obtaining the time course change in the feature point position is not limited to this. For example, the deviation (displacement) of the feature point between two sequential frames may be obtained in succession.

The movement detecting processor 232 sends control information for canceling (eliminating) the time course change to the scan controller 213 each time the time course change in the feature point position is calculated. The scan controller 213 corrects the orientation of the optical scanner 44 based on the control information input in a sequential manner.

The movement detecting processor 232 is implemented by the cooperation of hardware including a processor and movement detecting software.

<User Interface 240>

The user interface 240 includes the display device 241 and the operation device 242. The display device 241 includes the display device 3. The operation device 242 includes various kinds of operation devices and input devices. The user interface 240 may include, for example, a device such as a touch panel in which a display function and an operation function are integrated. It is also possible to construct an embodiment example that does not include at least part of the user interface 240. For example, the display device may be an external device connected to the ophthalmic imaging apparatus.

<Operation>

The operation of the ophthalmic imaging apparatus 1 will be described. Note that preparatory operations same as or similar to conventional preparatory operations have already been carried out prior to the operation example described below. The preparatory operations include, for example, input of a patient ID, presentation of a fixation target, adjustment of a fixation position, alignment, focus adjustment, OCT optical path length adjustment, and the like.

Figure 10:
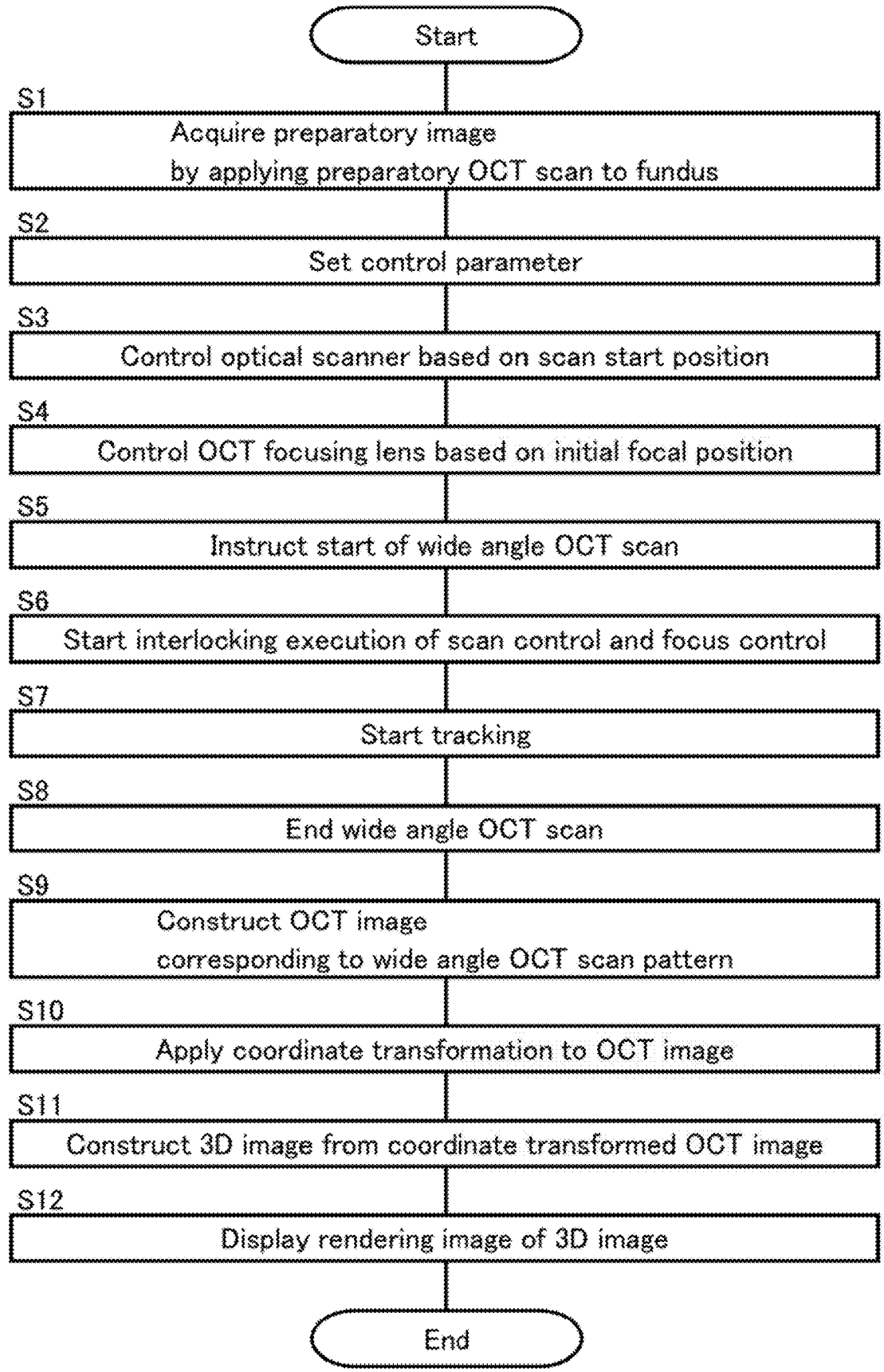
FIG. 10 is a flowchart illustrating an example of the operation of the ophthalmic imaging apparatus according to the embodiment example.

An example of the operation of the ophthalmic imaging apparatus 1 will be described with referring to FIG. 10.

(S1: Acquire Preparatory Image by Applying Preparatory OCT Scan to Eye Fundus)

First, the ophthalmic imaging apparatus 1 applies a preparatory OCT scan to the fundus Ef with elements including the optical scanner 44 and the OCT unit 100. The image constructing unit 220 constructs a preparatory image from data acquired by the preparatory OCT scan. The preparatory image is sent to the parameter setting processor 231.

(S2: Set Control Parameter)

The parameter setting processor 231 sets the focus control parameter based on the preparatory image obtained in the step S1. The determined control parameter is stored, for example, in the memory 212.

In the step S2 or in a stage prior to the step S2, the ophthalmic imaging apparatus 1 may perform setting of a wide angle OCT scan application area, setting of a central region, setting of a peripheral region, setting of a scan control parameter, and the like. Note that any of these conditions may be a fixed condition, may be a condition selected from a plurality of options, or may be a condition manually set by the user. The parameter setting processor 231 may execute the setting of the focus control parameter based on the result of these settings and the preparatory image.

The present example uses the central region 310 and the peripheral region 320 shown in FIG. 5A, the spiral scan pattern 510 shown in FIG. 8A, and the focus control parameter shown in FIG. 9A. Further, it is assumed here that the outer edge of the peripheral region 320 defines the outer edge of the wide angle OCT scan application area.

(S3: Control Optical Scanner Based on Scan Start Position)

The scan controller 213 determines a scan start position based on the scan control parameter set in or prior to the step S2, and controls the optical scanner 44 based on the scan start position determined. As a result of this, each galvano mirror in the optical scanner 44 is oriented toward the direction corresponding to the scan start position.

In the present example, typically, a fixation target corresponding to the fixation position for acquiring an image whose center is located at the macula is displayed on the LCD 39, and further the center of the wide angle OCT scan application area is placed at the macular center. If the alignment state and the fixation state of the subject's eye E are both appropriate, the macular center is located on the optical axis of the measurement arm. Therefore, in the present example, each galvano mirror of the optical scanner 44 is arranged in its neutral position.

(S4: Move OCT Focusing Lens Based on Initial Focal Position)

The focus controller 214 determines an initial focal position in the focus control based on the focus control parameter set in the step S2, and then controls the OCT focus driver 43A based on the initial focal position to move the OCT focusing lens 43.

In the present example, control of the OCT focus driver 43A is performed in such a manner that the focal position $\zeta_{11}$ corresponding to the scan start position n=0 shown in FIG. 9A is determined as the initial focal position, and that the OCT focusing lens 43 is placed at the position corresponding to the initial focal position $\zeta_{11}$.

Note that the control according to the step S4 may be executed before the control according to the step S3. Alternatively, the control according to the step S3 and the control according to the step S4 may be performed in parallel.

(S5: Instruct Start of Wide Angle OCT Scan)

After the completion of both the control according to the step S3 and the control according to the step S4, an instruction for starting the wide angle OCT scan is input to the scan controller 213 and the focus controller 214. The instruction may be issued manually by the user. Alternatively, the main controller 211 may issue the instruction automatically in response to having a predetermined condition satisfied, such as having completed both the control according to the step S3 and the control according to the step S4.

(S6: Start Interlocking Execution of Scan Control and Focus Control)

Upon receiving the start instruction in the step S5, the scan controller 213 and the focus controller 214 start controls in an interlocking manner, thereby starting the wide angle OCT scanning.

In the present example, the scan control by the scan controller 213 and the focus control by the focus controller 214 are executed based on the focus control parameter (the graph showing the relationship between the scan position "n" and the focal position "z") shown in FIG. 9A.

More specifically, the scan controller 213 performs control of the optical scanner 44 and control of the OCT unit 100 such that a A-scan is sequentially applied to a plurality of scan points (the scan position n=0 to N−1 shown in FIG. 9A) arranged along the spiral scan pattern 510 shown in FIG. 8A.

In parallel with this, the focus controller 214 performs control of the OCT focus driver 43A such that when an A-scan is applied to a scan position "n" shown in FIG. 9A, the OCT focusing lens 43 is to be placed at a position according to the focal position z=$\zeta(n)$ corresponding to that scan position "n".

As a result, the ophthalmic imaging apparatus 1 can perform scanning of the fundus Ef according to the spiral scan pattern 510 shown in FIG. 8A while performing movement of the focal position according to the focus control parameter shown in FIG. 9A.

(S7: Start Tracking)

In response to the start of the interlocking control in the step S6, or at an arbitrary timing before the start of the interlocking control, the ophthalmic imaging apparatus 1 starts tracking for correcting the projection position of the measurement light LS (application position of the A-scan) according to the movement of the subject's eye E. The tracking is performed in the above-described manner by using elements including the fundus camera unit 2, the movement detecting processor 232, and the scan controller 213. With the tracking, the spiral scan pattern 510 shown in FIG. 8A can be applied even in the case where the subject's eye E moves during the execution of the wide angle OCT scan.

(S8: End Wide Angle OCT Scan)

The ophthalmic imaging apparatus 1 ends the wide angle OCT scan started in the step S6 in response to the completion of an OCT scan along the spiral scan pattern 510 shown in FIG. 8A, for example.

Note that the OCT scan along the wide angle OCT scan pattern is performed a predetermined number of times (once or more). For example, the OCT scan along the spiral scan pattern 510 may be performed twice or more. In this case, the following processes may be executed in the next step S9: a process of constructing two or more OCT images respectively from two or more data sets respectively acquired by these two or more OCT scans; and a process of composing (synthesizing) the two or more OCT images constructed. Here, the image composition may be averaging.

(S9: Construct OCT Image Corresponding to Wide Angle OCT Scan Pattern)

The image constructing unit 220 constructs an OCT image from the data acquired by the wide angle OCT scan executed in the steps S6 to S8.

The spiral scan pattern 510 shown in FIG. 8A is typically defined using the two dimensional polar coordinate system $(r, \theta)$. With the two dimensional polar coordinate system $(r, \theta)$, the spiral scan pattern 510 is defined, for example, by the following formula: $x = \cos\theta - \theta \times \sin\theta$, $y = \sin\theta + \theta \times \cos\theta$.

In this case, the OCT image constructed in the step S9 is also defined using the two dimensional polar coordinate system $(r, \theta)$. In other words, the positions of the plurality of A-scan images constituting the OCT image constructed in the step S9 are defined with the two dimensional polar coordinate system $(r, \theta)$.

Figure 11:
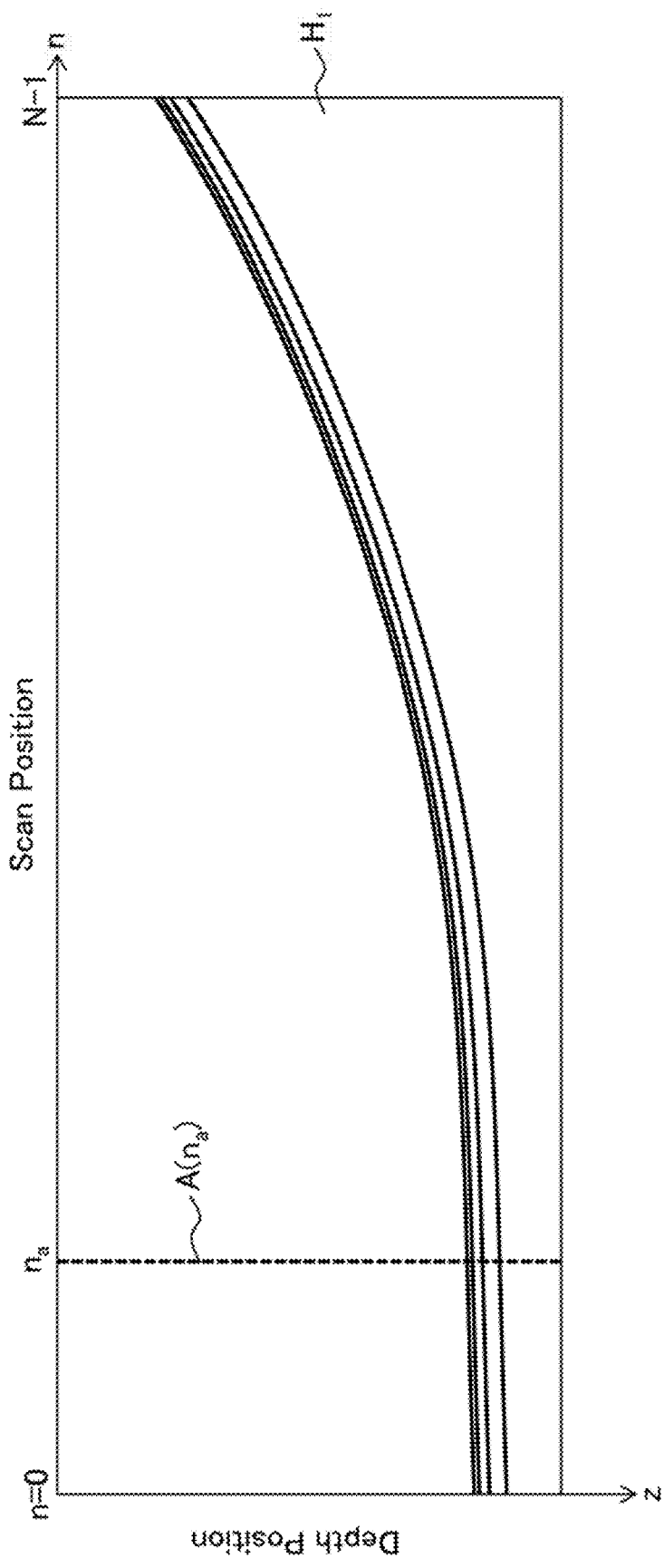
FIG. 11 is a schematic diagram for describing an example of the operation of the ophthalmic imaging apparatus according to the embodiment example.

In the present example, the positions of a plurality of A-scans disposed along the spiral scan pattern 510 shown in FIG. 8A correspond to the plurality of scan positions n=0 to N−1 shown in FIG. 9A, respectively. Therefore, the positions of the plurality of A-scan images constructed in the step S9 also correspond to the plurality of scan positions n=0 to N−1, respectively. For example, the OCT image $H_1$ shown in FIG. 11 is constructed by execution of the step S9. The OCT image $H_1$ is composed of the A-scan images $A(n_p)$ assigned to each scan position $n=n_p$. It should be noted that each scan position $n=n_p$ is defined using the two dimensional polar coordinate system $(r, \theta)$.

The definition formula of a spiral scan pattern is not limited to that of the present example, and the coordinate system that defines a wide angle OCT scan pattern and an OCT image is not limited to the two dimensional polar coordinate system of the present example.

(S10: Apply Coordinate Transformation to OCT Image)

The image constructing unit 220 applies a coordinate transformation to the OCT image constructed in the step S9.

For example, in the case of applying a wide angle OCT scan pattern that includes a curved scan pattern defined with a polar coordinate system whose origin is located at the center of an OCT scan application area, the image constructing unit 220 performs the following processes: a process of constructing an OCT image defined with the polar coordinate system from data acquired by an OCT scan applied to the subject's eye E according to the curved scan pattern (S9); and a process of converting the OCT image defined with the polar coordinate system to an image defined with the three dimensional Cartesian coordinate system (S10).

When the OCT image $H_1$ shown in FIG. 11 is constructed in the step S9, the image constructing unit 220 transforms the coordinates of each scan position $n=n_p$ defined in the two dimensional polar coordinate system $(r, \theta)$ to coordinates defined in the two dimensional Cartesian coordinate system $(x, y)$ in accordance with a coordinate transformation formula between the two dimensional polar coordinate system $(r, \theta)$ and the two dimensional Cartesian coordinate system $(x, y)$. The coordinate transformation formula is, for example, the above-mentioned formula: $(x=\cos\theta-\theta\times\sin\theta, y=\sin\theta+\theta\times\cos\theta)$.

Figure 12:
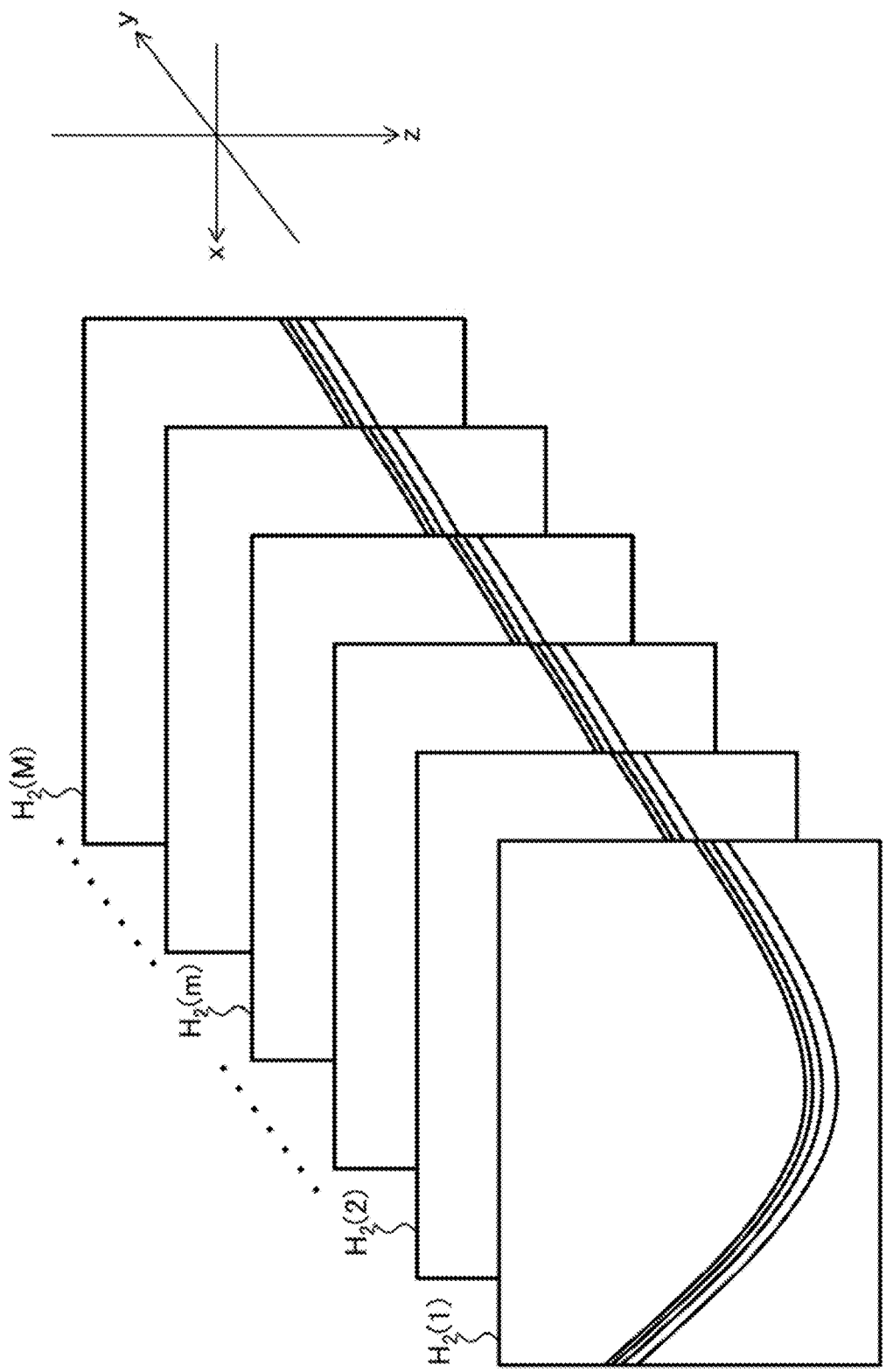
FIG. 12 is a schematic diagram for describing an example of the operation of the ophthalmic imaging apparatus according to the embodiment example.

Such a coordinate transformation yields a group of OCT images $H_2(m)$ (m=1, 2, ..., M) shown in FIG. 12, for example. Each OCT image $H_2(m)$ is a B-scan image along the x direction and is defined using the two dimensional Cartesian coordinate system $(x, z)$. Further, the M pieces of the OCT images $H_2(1)$ to $H_2(M)$ are arranged along the y direction. In this manner, the M pieces of the OCT images $H_2(1)$ to $H_2(M)$ are defined using the three dimensional Cartesian coordinate system $(x, y, z)$.

(S11: Construct Three Dimensional Image from Coordinate Transformed OCT Image)

The image constructing unit 220 can construct a three dimensional image from the OCT images after the coordinate transformation obtained in the step S10.

With the step S10 of the present example, the M pieces of the OCT images $H_2(1)$ to $H_2(M)$, which are stack data, may be obtained, for example. The image constructing unit 220 may then construct volume data by applying voxelization to the M pieces of the OCT images $H_2(1)$ to $H_2(M)$.

(S12: Display Rendering Image of Three Dimensional Image)

The image constructing unit 220 may apply rendering to the three dimensional image constructed in the step S11. The main controller 211 may display the rendering image obtained thereby on the display device 241.

<Actions and Effects>

Some actions and effects of some embodiment examples will be described.

The ophthalmic imaging apparatus (1) according to some embodiment examples includes a data acquiring unit, an image constructing unit, a focal position changing unit, a scan controller, and a focus controller.

The data acquiring unit is configured to acquire data by applying an OCT scan to a subject's eye (E). In the above example, the data acquiring unit includes the OCT unit 100 and the elements in the fundus camera unit 2 that constitutes the measurement arm (the retroreflector 41, the OCT focusing lens 43, the optical scanner 44, the objective lens 22, etc.).

The image constructing unit is configured to construct an image from the data acquired by the data acquiring unit. In the above example, the image constructing unit includes the image constructing unit 220.

The focal position changing unit is provided to an optical path of measurement light (measurement arm) projected onto the subject's eye (E) by the data acquiring unit, and is configured to change the position of the focal point of the measurement arm. In the above example, the focal position changing unit includes the OCT focusing lens 43 and the OCT focus driver 43A.

The scan controller is configured to control the data acquiring unit according to a scan pattern (wide angle OCT scan pattern) that includes a first partial pattern and a second partial pattern. The first partial pattern is a continuous scan pattern for a central region (310) of an OCT scan application area (wide angle OCT scan application area), and the second partial pattern is a continuous scan pattern for a peripheral region (320). In the above example, the scan controller includes the scan controller 213.

The focus controller is configured to control the focal position changing unit such that a first focal position is applied in parallel with an application of an OCT scan to at least a part of the first partial pattern. Further, the focus controller is configured to control the focal position change unit such that a second focal position different from the first focal position is applied in parallel with an application of an OCT scan to at least a part of the second partial pattern. In the above example, the focus controller includes the focus controller 214. Furthermore, in the above example, at least a part of the first partial pattern corresponds to at least a part of the central region 310, and the first focal position corresponds to, for example, the z coordinate $\zeta_{11}$ in FIG. 9A. In addition to this, in the above example, at least a part of the second partial pattern corresponds to at least a part of the peripheral region 320, and the second focal position corresponds to, for example, the z coordinate $\zeta_{12}$ in FIG. 9A.

The embodiment example configured in this way is capable of performing scanning of a pattern that includes the continuous first partial pattern for the central region and the continuous second partial pattern for the peripheral region. Taking the eyeball shape (the concave, curved shape of the eye fundus) into account, the central region is located in a relatively deep portion of the eyeball, and the peripheral region is located in a relatively shallow portion. Therefore, the focal position suitable for the central region and the focal position suitable for the peripheral region are different from each other. In the present embodiment example, in addition to the scan control according to the aforementioned scan pattern, the first focal position can be applied to the central region (the first partial pattern), and the second focal position can be applied to the peripheral region (the second partial pattern). This makes it possible to perform a wide angle OCT scan while moving the focal position at a practical speed. Therefore, according to the present embodiment example, it is possible to acquire a high quality OCT image while performing wide angle OCT scanning at a high speed.

It should be noted that some number of B-scans pass through both the central region and the peripheral region in the case of employing a raster scan as a wide angle OCT scan like conventional cases. It is practically impossible to switch and apply two or more focal positions that include the first focal position and the second focal position in parallel with performing such B-scans at a high speed.

In the present embodiment example, the scan pattern may include a curved scan pattern defined in a polar coordinate system whose origin is located at the center of the OCT scan application area.

For the setting of the curved scan pattern, for example, the structural characteristics and control characteristics of the optical scanner (44), the required scan speed, the required scan density, and the like may be taken into consideration.

In the present embodiment example, the curved scan pattern may be a spiral scan pattern (510) directed from the center to the outer edge of the OCT scan application area. Alternatively, the curved scan pattern may be a spiral scan pattern (520) directed from the outer edge to the center of the OCT scan application area.

Another example of a curved scan pattern is a concentric circular scan pattern.

In the present embodiment example, the image constructing unit (220) may be configured to construct an image defined in the polar coordinate system (the OCT image $H_1$) from data acquired by an OCT scan applied to the subject's eye (E) according to the curved scan pattern. Further, the image constructing unit (220) may be configured to convert the image defined in the polar coordinate system (the OCT image $H_1$) to an image defined in the three dimensional Cartesian coordinate system (the OCT image $H_2$ (m)).

According to such a configuration, it becomes possible to construct, from the OCT image obtained using the curved scan pattern, an OCT image defined with the three dimensional Cartesian coordinate system. Here, image processing and analysis can be easily carried out using the three dimensional Cartesian coordinate system.

In the present embodiment example, a first focal length corresponding to the first focal position to be applied to the central region (the first partial pattern) may be set longer than a second focal length corresponding to the second focal position to be applied to the peripheral region (the second partial pattern).

According to such a configuration, a wide angle OCT scan can be performed at a high speed while changing the focal position according to the shape of the eyeball, thereby making it possible to acquire a high quality OCT image.

The ophthalmic imaging apparatus (1) according to the present embodiment example may apply a preparatory OCT scan to the subject's eye (E) by the data acquiring unit prior to the application of the wide angle OCT scan according to the wide angle OCT scan pattern. In the case where the preparatory OCT scan has been performed, the image constructing unit (220) may construct a preparatory image (G) from data acquired by the preparatory OCT scan. Further, the parameter setting processor (231) of the ophthalmic imaging apparatus (1) according to the present embodiment example may execute setting of one or more focus control parameters based on the preparatory image (G) constructed by the image constructing unit (220). In addition, the focus controller (214) can perform control of the focal position changing unit according to the one or more focus control parameters set by the parameter setting processor (231).

Here, the focus control parameter may be, for example, a graph as shown in FIG. 9A, or may be a numerical value equal to or greater than 1. As an example of the latter, the focus control parameter may be a numerical value indicating the focal position, such as the z coordinates $\zeta_{11}$ and $\zeta_{12}$.

According to such a configuration, the focus control parameter can be determined based on the actual shape of the subject's eye (e.g., the shape of the eye fundus). This can achieve further improvement of the quality of an OCT image to be acquired.

In the present embodiment example, the one or more focus control parameters determined from the preparatory image may include a focal position change range that includes the first focal position and the second focal position. In the above example, for example, the focus control parameter of FIG. 9A includes the focal position change range $[\zeta_{12}, \zeta_{11}]$ as information.

According to such a configuration, it is possible to determine a range within which the focal position is changed, based on the preparatory image, that is, based on the actual shape of the subject's eye.

In the present embodiment example, the one or more focus control parameters determined from the preparatory image may include at least one of movement speed and movement acceleration of the focal position. In the above example, for example, the focus control parameter consisting of the smooth curve shown in FIG. 9A includes information on the movement speed of the focal position of the measurement arm as well as information on movement acceleration thereof.

According to such a configuration, the movement speed and the movement acceleration of the focal position can be determined based on the preparatory image, that is, based on the actual shape of the subject's eye.

The ophthalmic imaging apparatus (1) according to the present embodiment example may further include a photographing unit (the fundus camera unit 2) configured to repetitively photograph the subject's eye (E), and a movement detecting processor (232) configured to detect movement of the subject's eye by analyzing a time series image acquired by the photographing unit. Further, the data acquiring unit may include an optical scanner (44) configured to deflect light for OCT scanning. In addition, the scan controller (213) may control the optical scanner (44) based on an output from the movement detecting processor (232) in parallel with controlling the data acquiring unit on the basis of the wide angle OCT scan pattern.

According to such a configuration, a wide angle OCT scan can be conducted while performing tracking for correction of the projection position of the measurement light according to the movement of the subject's eye. As a result of this, the scanning according to the wide angle OCT scan pattern can be properly performed even if the subject's eye moves during the wide angle OCT scanning. In addition, interruption and reperformance of scanning can be avoided.

While the above example describes the case where an OCT scan is applied to the eye fundus (Ef), some embodiment examples may be implemented which are capable of achieving similar or same actions and effects for the anterior eye segment such as the cornea, crystalline lens, iris, corner angle, or the like. The focus control parameter can be determined according to the shape of the site to which OCT scanning is to be applied.

Some embodiment examples provide a method and technique of controlling an ophthalmic imaging apparatus. The ophthalmic imaging apparatus to which this control method is applied includes a data acquiring unit, an image constructing unit, and a focal position changing unit. The data acquiring unit is configured to acquire data by applying an OCT scan to the subject's eye. The image constructing unit is configured to construct an image from the data acquired, and the focal position changing unit is provided to an optical path of measurement light projected onto the subject's eye by the data acquiring unit.

The control method includes a scan control step and a focus control step. The scan control step is operated to control the data acquiring unit according to a scan pattern that includes a first partial pattern and a second partial pattern. The first partial pattern is a continuous scan pattern for a central region of an OCT scan application area and the second partial pattern is a continuous scan pattern for a peripheral region. The focus control step is operated to control the focal position changing unit such that a first focal position is applied in parallel with an application of an OCT scan to at least a part of the first partial pattern and a second focal position different from the first focal position is applied in parallel with an application of an OCT scan to at least a part of the second partial pattern.

It is possible to combine any of the matters and items described in the embodiment examples with the control method of the ophthalmic imaging apparatus.

Some embodiment examples provide a program that causes an ophthalmic imaging apparatus to execute the control method. The program can be combined with any of the matters and items described in the embodiment examples.

Further, it is possible to create a computer-readable non-transitory recording medium storing such a program. It is possible to combine any of the matters and items described in the embodiment examples with the recording medium. The non-transitory recording medium may have any form, and examples thereof include a magnetic disk, an optical disk, a magneto-optical disk, a semiconductor memory, and the like.

According to the method, the program, or the recording medium according to some embodiment examples, it is possible to acquire a high quality OCT image while performing a wide angle OCT scan at a high speed. In addition, actions and effects are exhibited according to matters and items combined with the method, the program, or the recording medium according to the embodiment examples.

The configuration described above is only an example of the embodiments of the present invention. Therefore, it is possible to make any modifications (e.g., omissions, substitutions, replacements, additions) within the scope of the gist of the present invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic imaging apparatus comprising:
    a data acquiring unit including an optical scanner and configured to acquire data by applying an optical coherence tomography (OCT) scan to a fundus of a subject's eye;
    an image constructing circuit configured to construct an image from the data acquired by the data acquiring unit;
    a focal position changing unit including a lens and provided to an optical path of measurement light projected onto the fundus by the data acquiring unit; and
    a controller, wherein the controller includes
        a scan controller circuit configured to control the data acquiring unit according to a wide angle OCT scan pattern that includes a first partial pattern and a second partial pattern, the first partial pattern being a continuous scan pattern for a central region of wide angle OCT scan application area of the fundus and the second partial pattern being a continuous scan pattern for a peripheral region, and
        a focus controller circuit configured to control the focal position changing unit such that a first focal position is applied in parallel with an application of an OCT scan to at least a part of the first partial pattern and a second focal position different from the first focal position is applied in parallel with an application of an OCT scan to at least a part of the second partial pattern, wherein
    the central region includes a macular center of the fundus, the peripheral region includes a peripheral part of the fundus, and a first focal length corresponding to the first focal position is longer than a second focal length corresponding to the second focal position.

2. The ophthalmic imaging apparatus of claim 1, wherein the wide angle OCT scan pattern is a continuous curved scan pattern defined in a polar coordinate system whose origin is located at a center of the wide angle OCT scan application area.

3. The ophthalmic imaging apparatus of claim 2, wherein the continuous curved scan pattern is one of a spiral scan pattern directed from the center to an outer edge of the wide angle OCT scan application area of the fundus and a spiral scan pattern directed from the outer edge to the center of the wide angle OCT scan application area of the fundus.

4. The ophthalmic imaging apparatus of claim 2, wherein the image constructing circuit constructs an image defined in the polar coordinate system from data acquired by an OCT scan applied to the fundus according to the continuous curved scan pattern, and converts the image defined in the polar coordinate system to an image defined in a three dimensional Cartesian coordinate system.

5. The ophthalmic imaging apparatus of claim 1, wherein the center of the wide angle OCT scan application area of the fundus is located at a macular center of the fundus.

6. The ophthalmic imaging apparatus of claim 1, wherein the data acquiring unit applies a preparatory OCT scan to the subject's eye prior to an OCT scan according to the wide angle OCT scan pattern, and the image constructing circuit constructs a preparatory image from data acquired by the preparatory OCT scan, and the ophthalmic imaging apparatus further comprising a parameter setting processor configured to perform setting of one or more focus control parameters based on the preparatory image constructed by the image constructing circuit, wherein the focus controller circuit performs control of the focal position changing unit according to the one or more focus control parameters set by the parameter setting processor.

7. The ophthalmic imaging apparatus of claim 6, wherein the one or more focus control parameters include a focal position change range that includes the first focal position and the second focal position.

8. The ophthalmic imaging apparatus of claim 6, wherein the one or more focus control parameters include at least one of movement speed and movement acceleration of a focal position.

9. The ophthalmic imaging apparatus of claim 1, further comprising:

a camera configured to perform repetitive photographing of the fundus; and a movement detecting processor configured to detect movement of the fundus by analyzing a time series image acquired by the camera, wherein the data acquiring unit includes the optical scanner configured to deflect light for OCT scanning, and the scan controller circuit controls the optical scanner based on an output from the movement detecting processor while controlling the data acquiring unit according to the wide angle OCT scan pattern.

10. A method of controlling an ophthalmic imaging apparatus that includes a data acquiring unit, an image constructing circuit, and a focal position changing unit, the data acquiring unit being configured to acquire data by applying an optical coherence tomography (OCT) scan to a fundus of a subject's eye, the image constructing circuit being configured to construct an image from the data acquired by the data acquiring unit, and the focal position changing unit being provided to an optical path of measurement light projected onto the fundus by the data acquiring unit, the method comprising:

a scan control step of controlling the data acquiring unit according to a wide angle OCT scan pattern that includes a first partial pattern and a second partial pattern, the first partial pattern being a continuous scan pattern for a central region of a wide angle OCT scan application area of the fundus and the second partial pattern being a continuous scan pattern for a peripheral region; and a focus control step of controlling the focal position changing unit such that a first focal position is applied in parallel with an application of an OCT scan to at least a part of the first partial pattern and a second focal position different from the first focal position is applied in parallel with an application of an OCT scan to at least a part of the second partial pattern, wherein the central region includes a macular center of the fundus, the peripheral region includes a peripheral part of the fundus, and a first focal length corresponding to the first focal position is longer than a second focal length corresponding to the second focal position.

11. A computer-readable non-transitory recording medium storing a program causing a computer to execute the method of controlling the ophthalmic imaging apparatus of claim 10.

* * * * *